US011590210B2

(12) United States Patent
McCarty et al.

(10) Patent No.: US 11,590,210 B2
(45) Date of Patent: Feb. 28, 2023

(54) METHODS FOR DELIVERY OF POLYNUCLEOTIDES BY ADENO-ASSOCIATED VIRUS FOR LYSOSOMAL STORAGE DISORDERS

(71) Applicant: NATIONWIDE CHILDREN'S HOSPITAL, INC., Columbus, OH (US)

(72) Inventors: Douglas M. McCarty, Pataskala, OH (US); Haiyan Fu, Pataskala, OH (US)

(73) Assignee: NATIONWIDE CHILDREN'S HOSPITAL, INC., Columbus, OH (US)

(*) Notice: Subject to any disclaimer, the term of this patent is extended or adjusted under 35 U.S.C. 154(b) by 0 days.

(21) Appl. No.: 16/293,196

(22) Filed: Mar. 5, 2019

(65) Prior Publication Data
US 2020/0000887 A1    Jan. 2, 2020

Related U.S. Application Data

(63) Continuation of application No. 13/491,326, filed on Jun. 7, 2012, now abandoned.

(60) Provisional application No. 61/494,635, filed on Jun. 8, 2011.

(51) Int. Cl.
| | |
|---|---|
| *A61K 48/00* | (2006.01) |
| *C12N 9/14* | (2006.01) |
| *A61K 38/46* | (2006.01) |
| *C12N 15/86* | (2006.01) |
| *A61K 35/761* | (2015.01) |
| *A61K 47/26* | (2006.01) |
| *C12N 7/00* | (2006.01) |

(52) U.S. Cl.
CPC ............ *A61K 38/46* (2013.01); *A61K 35/761* (2013.01); *A61K 47/26* (2013.01); *A61K 48/005* (2013.01); *C12N 7/00* (2013.01); *C12N 9/14* (2013.01); *C12N 15/86* (2013.01); *C12N 2750/14121* (2013.01); *C12N 2750/14143* (2013.01); *C12N 2750/14171* (2013.01); *C12Y 310/01001* (2013.01)

(58) Field of Classification Search
None
See application file for complete search history.

(56) References Cited

U.S. PATENT DOCUMENTS

| | | |
|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,566,118 B1 | 5/2003 | Atkinson et al. |
| 6,582,692 B1 | 6/2003 | Podsakoff et al. |
| 6,841,357 B1 | 1/2005 | Vaillancourt et al. |
| 7,198,951 B2 | 4/2007 | Gao et al. |
| 7,906,111 B2 | 3/2011 | Wilson et al. |
| 8,999,948 B2 | 4/2015 | Tubert et al. |
| 9,415,121 B2 | 8/2016 | Kaspar et al. |
| 9,725,716 B2 | 8/2017 | Burghes et al. |
| 9,926,574 B2 | 3/2018 | Barkats |
| 10,208,318 B2 | 2/2019 | Barkats |
| 10,301,648 B2 | 5/2019 | Vandenberghe et al. |
| 10,738,326 B2 | 8/2020 | Muramatsu |
| 2003/0083299 A1 | 5/2003 | Ferguson |
| 2003/0118556 A1 | 6/2003 | Kaspar et al. |
| 2004/0076613 A1 | 4/2004 | Mazarakis et al. |
| 2005/0014262 A1 | 1/2005 | Gao et al. |
| 2005/0053922 A1 | 3/2005 | Schaffer et al. |
| 2007/0036760 A1 | 2/2007 | Wilson et al. |
| 2007/0280906 A1 | 12/2007 | Petras |
| 2008/0176799 A1 | 7/2008 | Ferguson et al. |
| 2009/0162332 A1 | 6/2009 | Davidson et al. |

(Continued)

FOREIGN PATENT DOCUMENTS

| | | |
|---|---|---|
| EP | 1620133 A1 | 2/2006 |
| JP | 2007-527427 A | 9/2007 |

(Continued)

OTHER PUBLICATIONS

Fu et al Molecular Therapy, 2011, 19(6), 1025-1033, published online, Mar. 8, 2011 (Year: 2011).*
Fu et al , Molecular Genetics and Metabolism, (Feb. 2011) vol. 102, No. 2, pp. S18-S19. Abstract No. 118. Meeting Info: 7th Annual Research Meeting of the Lysosomal Disease Network, WORLD Symposium. Las Vegas, NV (abstract only), p. 1. (Year: 2011).*
Fu et al Molecular Therapy, (May 2011) vol. 19, Supp. Suppl. 1, pp. S131. Abstract No. 337. Meeting Info: 14th Annual Meeting of the American Society of Gene and Cell Therapy. Seattle, WA, United States. , abstract only p. 1 (Year: 2011).*
Cressant et al The Journal of Neuroscience, Nov. 10, 24(45):10229-10239 (Year: 2004).*

(Continued)

*Primary Examiner* — Anoop K Singh
(74) *Attorney, Agent, or Firm* — Marshall, Gerstein & Borun LLP

(57) ABSTRACT

The present invention relates to methods and materials useful for systemically delivering polynucleotides across the blood brain barrier using adeno-associated virus as a vector. For example, the present invention relates to methods and materials useful for systemically delivering α-N-acetylglucosaminidase polynucleotides to the central and peripheral nervous systems, as well as the somatic system. Use of these methods and materials is indicated, for example, for treatment of the lysosomal storage disorder mucopolysaccharidosis IIIB. As another example, the present invention relates to methods and materials useful for systemically delivering N-sulphoglucosamine sulfphohydrolase polynucleotides to the central and peripheral nervous systems, as well as the somatic system. Use of this second type of methods and materials is indicated, for example, for treatment of the lysosomal storage disorder mucopolysaccharidosis IIIA.

7 Claims, 11 Drawing Sheets

Specification includes a Sequence Listing.

(56) References Cited

U.S. PATENT DOCUMENTS

| | | | |
|---|---|---|---|
| 2009/0202490 A1 | 8/2009 | Schaffer et al. | |
| 2010/0130594 A1 | 5/2010 | Barkats | |
| 2010/0240739 A1* | 9/2010 | Barkats | A61P 37/02 514/44 R |
| 2012/0177605 A1* | 7/2012 | Kaspar | A61P 21/00 424/93.2 |
| 2013/0039888 A1 | 2/2013 | McCarty et al. | |
| 2013/0158104 A1* | 6/2013 | Tubert | A61K 48/0066 514/44 R |
| 2013/0195800 A1 | 8/2013 | Roeth et al. | |
| 2013/0195801 A1 | 8/2013 | Gao et al. | |
| 2013/0224836 A1 | 8/2013 | Muramatsu | |
| 2013/0225666 A1 | 8/2013 | Kaspar et al. | |
| 2013/0296532 A1 | 11/2013 | Hermens et al. | |
| 2013/0302308 A1 | 11/2013 | Ballabio et al. | |
| 2015/0252384 A1 | 9/2015 | Kaspar et al. | |
| 2016/0038613 A1 | 2/2016 | Kaspar et al. | |
| 2017/0216458 A1 | 8/2017 | Kaspar et al. | |
| 2018/0036431 A1 | 2/2018 | Kaspar et al. | |

FOREIGN PATENT DOCUMENTS

| | | |
|---|---|---|
| JP | 2007-528424 A | 10/2007 |
| WO | WO-1995/13365 A1 | 5/1995 |
| WO | WO-1995/13392 A1 | 5/1995 |
| WO | WO-1996/17947 A1 | 6/1996 |
| WO | WO-1997/06243 A1 | 2/1997 |
| WO | WO-1997/08298 A1 | 3/1997 |
| WO | WO-1997/08308 A1 | 3/1997 |
| WO | WO-1997/09441 A2 | 3/1997 |
| WO | WO-1997/21825 A1 | 6/1997 |
| WO | WO-1998/09657 A3 | 4/1998 |
| WO | WO-1999/11764 A3 | 6/1999 |
| WO | WO-2001/83692 A3 | 3/2002 |
| WO | WO-2002/081634 A2 | 10/2002 |
| WO | WO-2005/033321 A2 | 4/2005 |
| WO | WO-2005/056807 A2 | 6/2005 |
| WO | WO-2005/084713 A2 | 9/2005 |
| WO | WO-2005/087272 A2 | 9/2005 |
| WO | WO-2007/089632 A2 | 8/2007 |
| WO | WO-2008/154198 A1 | 12/2008 |
| WO | WO-2009/013290 A1 | 1/2009 |
| WO | WO-2009/043936 A1 | 4/2009 |
| WO | WO-2009/137006 A3 | 2/2010 |
| WO | WO-2010/071832 A1 | 6/2010 |
| WO | WO-2010/0129021 A1 | 11/2010 |
| WO | WO-2011/112902 A2 | 9/2011 |
| WO | WO-2011/133890 A1 | 10/2011 |
| WO | WO-2012/057363 A1 | 5/2012 |
| WO | WO-2019/108856 A1 | 6/2019 |
| WO | WO-2019/108857 A1 | 6/2019 |

OTHER PUBLICATIONS

Manfredsson et al Molecular Therapy, 17, 403-405 (Year: 2009).*
Ruzo et al XVIII Annual Congress of the European Society of Gene and Cell Therapy: 1389, abstract Or 96, Oct. 22-25, (Year: 2010).*
Zincarelli et al (Molecular Therapy,, 16, 1073-1080 (Year: 2008).*
MaCarty et al Gene Ther 8:1248-1254 (Year: 2001).*
NCBI accession No. U43573.1 , pp. 1-2 (Year: 1996).*
Sequence alignment of SEQ ID No. 1 vs accession No. U43573.1, pp. 1-3 (Year: 2021).*
Grimm et al Human Gene therapy, 2445-2450 (Year: 1999).*
Fu et al Molecular Therapy, 854, vol. 11, Supplement 1, S332 (Year: 2005).*
Fu et al Gene Therapy 14, 1065-1077 (Year: 2007).*
NCBI Accession No. U30894.1, dated Feb. 2, 1996 (2 pages).
Xiao et al., Gene therapy vectors based on adeno-associated virus type 1, *J. Virol.* 73:3994-4003 (1999).
Bevan et al., Early heart failure in the SMNDelta7 model of spinal muscular atrophy and correction by postnatal scAAV9-SMN delivery, *Hum. Mol. Genet.* 19:3895-905 (2010).
Bhaumik et al., A mouse model for mucopolysaccharidosis type III A (Sanfilippo syndrome), *Glycobiology.* 9(12):1389-1396 (1999).
Carter, Adeno-associated virus vectors, *Current Opinions in Biotechnology.* 533-539 (1992).
Clark et al., A stable cell line carrying adenovirus-inducible rep and cap genes allows for infectivity titration of adeno-associated virus vectors, *Gene Therapy.* 3:1124-1132 (1996).
Clark et al., Highly purified recombinant adeno-associated virus vectors are biologically active and free of detectable helper and wild-type viruses, *Hum. Gene Ther.* 10(6): 1031-1039 (1999).
Cressant et al., Improved behavior and neuropathology in the mouse model of Sanfilippo type IIIB disease after adeno-associated virus-mediated gene transfer in the striatum, *J. Neurosci.* 24:10229-10239 (2004).
De et al., High levels of persistent expression of $\alpha$1-antitrypsin mediated by the nonhuman primate serotype rh.10 adeno-associated virus despite preexisting immunity to common human adeno-associated viruses, *Mol. Ther.* 13(1): 67-76 (2006).
De Jong et al., Dimethylmethylene blue-based specrophotometry of glycosaminoglycans in untreated urng: a rapid screening procedure for mucopolysaccharidoses, *Clin. Chem.* 35: 1472-1477 (1989).
Duque et al., Intravenous administration of self-complementary AAV9 enables transgene delivery to adult motor neurons, *Mol. Ther.* 17: 1187-1196 (2009).
Foust et al., Intravascular AAV9 preferentially targets neonatal neurons and adult astrocytes, *Nature Biotechnology.* 27: 59-65 (2009).
Foust et al., Rescue of the spinal muscular atrophy phenotype in a mouse model by early postnatal delivery of SMN, *Nature Biotechnology.* 28:271-276 (2010).
Fraldi et al., Functional correction of CNS lesions in an MPS-IIIA mouse model by intracerebral AAV-mediated delivery of sulfamidase and SUMF1 genes, *Hum. Mol. Genet.* 16: 2693-2702 (2007).
Fu et al., Correction of Neurological Disease of Mucopolysaccharidosis IIIB in Adult Mice by rAAV9 Trans-Blood-Brain Barrier Gene Delivery, *Molecular Therapy.* 19:1025-1033 (2011).
Fu et al., Neurological correction of lysosomal storage in a mucopolysaccharidosis IIB mouse model by adeno-associated virus-mediated gene delivery, *Mol. Ther.* 5: 42-49 (2002).
Fu et al., Restoration of central nervous system $\alpha$-N-acetylglucosaminidase activity and therapeutic benefits in mucopolysaccharidosis IIB mice by a single intracisternal recombinant adeno-associated virus type 2 vector delivery, *J. Gene Med.* 12: 624-633 (2010).
Fu et al., Significantly increased lifespan and improved behavioral performances by rAAV gene delivery in adult mucopolysaccharidosis IIIB mice, *Gene Ther.*14: 1065-1077 (2007).
Fu et al., Molecular Genetics and Metabolism, (Feb. 2011) vol. 102, No. 2, pp. S18-S19. Abstract No. 118. Meeting Info: 7th Annual Research Meeting of the Lysosomal Disease Network, WORLD Symposium 2011, Las Vegas, NV (abstract only) page 1.
Fu et al., Molecular Therapy, (May 2011) vol. 19, Supp. Suppl. 1, pp. S131. Abstract No. 337. Meeting Info: 14th Annual Meeting of the American Society of Gene and Cell Therapy. Seattle, WA. USA. May 18, 2011-May 21, 2011, abstract only page 1.
Fu et al., Self-complementary adeno-associated virus serotype 2 vector: Global distribution and broad dispersion of AAV-mediated transgene expression in mouse brain. *Molec. Ther.* 8: 911-7 (2003).
Gao et al., Clades of adeno-associated viruses are widely disseminated in human tissues, *J. Virol.* 78:6381-6388 (2004).
GenBank Accession No. AF085716.
GenBank Accession No. AX753249.
GenBank Accession No. NC_00 1862.
GenBank Accession No. NC_001401.
GenBank Accession No. NC_001829.
GenBank Accession No. NC_002077.
GenBank Accession Nos. AX753246.
Guide for the Care and Use of Laboratory Animals [DHHS Publication No. (NIH) 85-23].
Hartung et al., Correction of metabolic, craniofacial, and neurologic abnormalities in MPS I mice treated at birth with adeno-associated virus vector transducing the human $\alpha$-L-Iduronidase gene, *Mol. Ther.* 9: 866-875 (2004).

(56) References Cited

OTHER PUBLICATIONS

Heldermon et al., Therapeutic efficacy of bone marrow transplant, intracranial AAV-mediated gene therapy, or both in the mouse model of MPS IIIB, *Mol. Ther*. 18: 873-880 (2010).
Hermonat et al., Use of adeno-associated virus as a mammalian DNA cloning vector: transduction of neomycin resistance into mammalian tissue culture cells, *Proc. Natl. Acad. Sci. USA*. 81:6466-6470 (1984).
Kaplitt et al., Safety and tolerability of gene therapy with an adeno-associated virus (AAV) borne GAD gene for Parkinson's disease: an open label, phase I trial, *Lancet*. 369: 2097-2105 (2007).
Laughlin et al., Cloning of infectious adeno-associated virus genomes in bacterial plasmids, *Gene*. 23:65-73 (1983).
Lebkowski et al., Adeno-associated virus: a vector system for efficient introduction and integration of DNA into a variety of mammalian cell types, *Mol. Cell. Biol*. 7:3988-3996 (1988).
Lehninger, Chapter 4. The amino acid building blocks of proteins, Biochemistry, 2nd Edition; Worth Publishers, Inc., New York, pp. 71-77 (1975).
Li et al., Mouse model of sanfilippo syndrome type B produced by targeted disruption of the gene encoding α-N-acetylglucosaminidase, *Proc. Natl. Acad. Sci. USA*. 96: 14505-14510 (1999).
Lijam et al., Social interaction and sensorimotor gating abnormalities in mice lacking Dvl1, *Cell*. 90:895-905 (1997).
Manfredsson et al., AAV9: A potential blood-brain barrier buster. *Molec. Ther*. 17: 403-5 (2009).
Marks et al., Safety and tolerability of intraputaminal delivery of CERE-120 (adeno-associated virus serotype 2-neurturin) to patients with idiopathic Parkinson's disease: an open-label, phase I trial, *Lancet Neurol*. 7:400-408 (2008).
McCarty et al., Mannitol-facilitated CNS entry of rAAV2 vector significantly delayed the neurological disease progression in MPS IIIB mice, *Gene Ther*. 16:1340-1352 (2009).
McLaughlin et al., Adeno-associated virus general transduction vectors: analysis of proviral structures, *J. Virol*. 62:1963-1973 (1988).
Mingozzi et al., Therapeutic in vivo gene transfer for genetic disease using AAV: progress and challenges, *Nat. Rev. Genet*. 12:341-55 (2011).
Mori et al., Two novel adeno-associated viruses from cynomolgus monkey: pseudotyping characterization of capsid protein, *Virology*. 330(2): 375-383 (2004).
Muzyczka, Use of adeno-associated virus as a general transduction vector for mammalian cells, *Current Topics in Microbiology and Immunology*. 158: 97-129 (1992).
Pacak et al., Recombinant adeno-associated virus serotype 9 leads to preferential cardiac transduction in vivo, *Circ. Res*. 99(4): 3-9 (2006).
Palli et al., Improved ecdysone receptor-based inducible gene regulation system, *Eur J. Biochem*. 270: 1308-1315 (2003).
Paul et al., Increased viral titer through concentration of viral harvests from retroviral packaging lines, *Human Gene Therapy*. 4:609-615 (1993).
Perrin et al., An experimental rabies vaccine produced with a new BHK-21 suspension cell culture process: use of serum-free medium and perfusion-reactor system, *Vaccine*. 13:1244-1250 (1995).
Ruffing et al., Mutations in the carboxy terminus of adeno-associated virus 2 capsid proteins affect viral infectivity: lack of an RGD integrin-binding motif, *J. Gen. Virol*. 75: 3385-3392 (1994).
Ruzo et al., Liver production of sulfamidase reverses peripheral and ameliorates CNS pathology in mucopolysaccharidosis IIIA mice, *Mol. Therap*. 20(2): 254-266 (2012).
Ruzo et al., XVIII Annual Congress of the European Society of Gene and Cell Therapy: 1389 (Abstract Or 96) (Oct. 22-25, 2010).
Sambrook et al., Molecular Cloning: A Laboratory Manual (Second ed., Cold Spring Harbor Laboratory Press, 1989), "Hybridization of radiolabeled probes to immobilized nucleic acids", §§ 9.47-9.51.
Samulski et al., Cloning of adeno-associated virus into pBR322: Rescue of intact virus from the recombinant plasmid in human cells, *Proc. Natl. Acad. S6. USA*. 79:2077-2081 (1982).
Samulski et al., Helper-free stocks of recombinant adeno-associated viruses: normal integration does not require viral gene expression, *J. Virol*. 63:3822-3828 (1989).
Sands et al., CNS-directed gene therapy for lysosomal storage diseases, *Acta Paediatr. Suppl*. 97: 22-27 (2008).
Sands et al., Percutaneous intravenous injection in neonatal mice, *Lab. Anim. Sci*. 49: 328-330 (1999).
Schenpp and Clark, Highly purified recombinant adeno-associated virus vectors, *Methods Mol. Med*. 69: 427-443 (2002).
Senapathy & Carter, Molecular Cloning of adeno-associated virus variant genomes and generation of infectious virus by recombination in mammalian cells, *J. Biol. Chem*. 259:4661-4666 (1984).
Srivastava et al., Nucleotide sequence and organization of the adeno-associated virus 2 genome, *J. Virol*. 45: 555-564 (1983).
Suzuki et al., Are animal models useful for understanding the pathophysiology of lysosomal storage disease? *Acta. Paediatr. Suppl*. 92:54-62 (2003).
Tratschin et al., A human parvovirus, adeno-associated virus, as a eucaryotic vector: transient expression and encapsidation of the procaryotic gene for chloramphenical acetyltransferase, *Mol. Cell. Biol*. 4:2072-2081 (1984).
Tratschin et al., Adeno-associated virus vector for high-frequency integration, expression, and rescue of genes in mammalian cells, *Mol. Cell. Biol*. 5:3251-3260 (1985).
Urlinger et al., Exploring the sequence space for tetracycline-dependent transcriptional activators: novel mutations yield expanded range and sensitivity, *Proc. Natl. Acad. Sci. USA*. 97(14):7963-7968 (2000).
Van de Lest et al., Quantification and characterization of glycosaminoglycans at the Nanogram level by a combined azure A-silver staining in agarose gels, *Anal. Biochem*. 221: 356-361 (1994).
Verma et al., Routes of drug administration, *International Journal of Pharmaceutical Studies and Research*. 1:54-9 (2010).
Walkley, Cellular pathology of lysosomal storage disorders, *Brain Pathol*. 175-93 (1998).
Wang et al., Adeno-associated virus serotype 8 efficiently delivers genes to muscle and heart, *Nature Biotech*. 23(3): 321-328 (2005).
Warburton et al., The conjoint importance of the hippocampus and anterior thalamic nuclei for allocentric spatial learning: evidence from a disconnection study in the rat, *J. Neurosci*. 21: 7323-7330 (2001).
Worgall et al., Treatment of late infantile neuronal ceroid lipofuscinosis by CNS administration of a serotype 2 adeno-associated virus expressing CLN2 cDNA, *Hum Gene Therapy*. pp. 1-12F (2008).
Zincarelli et al., Analysis of AAV serotypes 1-9 mediated gene expression and tropism in mice after systemic injection, *Mol. Ther*. 16:1073-80 (2008).
Zolotukhin et al., Recombinant adeno-associated virus purification using novel methods improves infectious titer and yield, *Gene Ther*. 6: 973-985 (1999).
Gray et al., Preclinical Differences of Intravascular AAV9 Delivery to Neurons and Glia: A Comparative Study of Adult Mice and Nonhuman Primates, Molecular Therapy. 19(6):1058-69 (2011).
McCarty et al., Adeno-associated virus terminal repeat (TR) mutant generates self-complementary vectors to overcome the rate-limiting step to transduction in vivo, Gene Therapy. 10(26):2112-8 (2003).
McCarty et al., Self-complementary recombinant adeno-associated virus (scAAV) vectors promote efficient transduction independently of DNA synthesis, Gene Therapy. 8(16):1248-54 (2001).
Zhang et al., Several rAAV Vectors Efficiently Cross the Blood-brain Barrier and Transduce Neurons and Astrocytes in the Neonatal Mouse Central Nervous System, The American Society of Gene and Cell Therapy. 19:1440-8 (2011).
Akbar et al., The role of MR myelography with intrathecal gadolinium in localization of spinal CSF leaks in patients with spontaneous intracranial hypotension, *AJNR Am. J. Neuroradiol*. 33:535-40 (2012).
Amicus Therapeutics, Amicus establishes gene therapy pipeline for Lysosomal storage disorders (LSDs). Sep. 20, 2018, p. 1-27 (2018).
Bowerman et al., Therapeutic strategies for spinal muscular atrophy: SMN and beyond, *Disease Models & Mechanisms*. 10:943-54 (2017).

(56) References Cited

OTHER PUBLICATIONS

Dayton et al., The advent of AAV9 expands applications for brain and spinal cord gene delivery, *Expert Opin. Biol. Ther.* 12:757-66 (2012).
De los Reyes et al., Abstract #204. Interim Results from the First Clinical Gene Therapy Trial for CLN6 Batten Disease. Forty-Eighth National Meeting of the Child Neurology Society. Charlotte, NC. Oct. 23-26, 2019.
Drory et al., EEG Recordings Following Intrathecal Iohexol Administration, *Clinical Neuropharmacology*, 13(4):318-21 (1990).
Gao et al., Mutations in a novel CLN6-encoded transmembrane protein cause variant neuronal ceroid lipofuscinosis in man and mouse, *Am. J. Hum. Genet*. 70:324-35 (2002).
Haria et al., Iohexol a review of its pharmacological properties and use as a contrast medium in Myelography and Neuroangiography, *CNS Drugs*. 7:229-55 (1997).
Highlights of Prescribing Information Omnipaque-iohexol injection, GE Healthcare Inc. (May 2018).
Hudry et al., Therapeutic AAV gene transfer to the nervous system: A clinical reality, Neuron 101: 839-62 (Mar. 6, 2019).
Olsen et al., Intrathecal iohexol-distribution following cervical myelography, postmyelographic registration of adverse effects, psychometric assessment and electroencephalographic recording, *Acta Neurol. Scand.*, 82: 321-8 (1990).
Papisov et al., Physiology of the intrathecal bolus: the leptomeningeal route for macromolecule and particle delivery to CNS, *Mol. Pharm*. 10: 1522-32 (2013).
Ratcliff et al., Cognitive and affective changes after myelography: A Comparison of Metrizamide and Iohexol, *Am. J. Roentgenol.*, 147:777-81 (1986).
Schuster et al., Biodistribution of adeno-associated virus serotype 9 (AAV9) vector after intrathecal and intravenous delivery in mouse, *Front Neuroanat*. 8:42 (2014).
Steinfeld et al., Late Infantile Neuronal Ceroid Lipofuscinosis: Quantitative Description of the Clinical Course in Patients With CLN2 Mutations, Am. J. Med. Genetics, 112:347-54 (2002).
Su et al., Real-time MR imaging with Gadoteridol predicts distribution of transgenes after convection-enhanced delivery of AAV2 vectors, *Mol. Ther*. 18:1490-5 (2010).
Vestergaard et al., Central Nervous System Reactions to Cervical Myelography, Acta Radiol. 32:411-4 (1999).
Wang et al., Expansive gene transfer in the rat CNS rapidly produces amyotrophic lateral sclerosis relevant sequelae when TDP-43 is overexpressed, *Mol. Ther*. 18:2064-74 (2010).
Carty et al., Convection-Enhanced Delivery and Systemic Mannitol Increase Gene Products Distribution of AAV Vectors 5, 8, and 9 and Increase Gene Product in the Adult Mouse Brain, *J Nuerosci Methods*. 194(1): 144-53 (2010).
Dehouck et al., An easier, reproducible, and mass-production method to study the blood-brain barrier in vitro, J. *Neurochem.*, 54(5):1798-801 (1990).
Del Gaudio et al., Increased MECP2 gene copy number as the result of genomic duplication in neurodevelopmentally delayed males, Genet. *Med.*, 8(12):784-92 (2006).
Dodge et al., Delivery of AAV-IGF-1 to the CNS extends survival in ALS mice through modification of aberrant glial cell activity, *Mol. Ther.*, 16(6):1056-64 (2008).
Eck et al., Gene-based therapy, Chapter 5 pp. 77-101, In: Goodman & Gilman's The Pharmacological Basis of Therapeutics, New York, NY: McGraw Hill (1996).
Examination Report, Australian patent application No. 2013296425, dated May 22, 2017.
Federici et al., Robust spinal motor neuron transduction following intrathecal delivery of AAV9 in pigs, *Gene Ther.*, 19(8):852-9 (2012).
Ford, Selected maturational changes observed in the postnatal rat brain, *Prog. Brain Res.*, 40(0):1-12 (1973).
Friez et al., Recurrent infections, hypotonia, and mental retardation caused by duplication of MECP2 and adjacent region in Xq28, *Pediatrics*, 118(6):e1687-95 (2006).

Gadalla et al., Improved survival and reduced phenotypic severity following AAV9/MECP2 gene transfer to neonatal and juvenile male Mecp2 knockout mice, *Mol. Ther.*, 21(1):18-30 (2013).
Gavrilina et al., Neuronal SMN expression corrects spinal muscular atrophy in severe SMA mice while muscle-specific SMN expression has no phenotypic effect, *Hum. Mol. Genet.*, 17(8):1063-75 (2008).
Grady et al., Cerebellar synaptic defects and abnormal motor behavior in mice lacking alpha- and beta-dystrobrevin, *J. Neurosci.*, 26(11):2841-51 (2006).
Gray et al., Directed evolution of a novel adeno-associated virus (AAV) vector that crosses the seizure-comprised blood-brain barrier (BBB), *Mol. Ther.*, 18:570-578 (2010).
Gray et al., Gene Therapy and neurodevelopmental disorders, *Neuropharmacology*, 68:136-142 (2012).
Gray et al., Viral vectors and delivery strategies for CNS gene therapy, *Ther. Deliv.*, 1:1-29 (2010).
Grossman et al., A randomized comparison of iodixanol and iohexol in adult intracranial computed tomography scanning, *Acad. Radiol.*, 3 Suppl 3:S488-94 (1996).
Guy et al., A mouse Mecp2-null mutation causes neurological symptoms that mimic Rett syndrome, *Nat. Genet.*, 27(3):322-6 (2001).
Guy et al., Reversal of neurological defects in a mouse model of Rett syndrome, *Science*, 315(5815):1143-7 (2007).
Haseloff et al., In search of the astrocytic factor(s) modulating blood-brain barrier functions in brain capillary endothelial cells in vitro, *Cell Mol. Neurobiol.*, 25(1):25-39 (2005).
Hawkins et al., The blood-brain barrier/neurovascular unit in health and disease, *Pharmacol. Rev.*, 57(2):173-85 (2005).
Hayashi et al., Induction of various blood-brain barrier properties in non-neural endothelial cells by close apposition to co-cultured astrocytes, *Glia*, 19(1):13-26 (1997).
Hsieh-Li et al., A mouse model for spinal muscular atrophy, *Nat. Genet.*, 24(1):66-70 (2008).
Hutson et al., Corticospinal tract transduction: a comparison of seven adenoassociated viral vector serotypes and a non-integrating lentiviral vector, *Gene Therapy*, 19:49-60 (2011).
Iadecola, Neurovascular regulation in the normal brain and in Alzheimer's disease, *Nat. Rev. Neurosci.*, 5(5):347-60 (2004).
Inagaki et al., Robust systemic transduction with AAV9 vectors in mice: efficient global cardiac gene transfer superior to that of AAV8, *Mol. Ther.*, 14(1):45-53 (2006).
International Application No. PCT/US09/68818, International Search Report and Written Opinion, dated Mar. 2, 2010.
International Application No. PCT/US13/53065, International Preliminary Report on Patentability, dated Feb. 3, 2015.
International Application No. PCT/US13/53065, International Search Report and Written Opinion, dated Sep. 2, 2013.
International Application No. PCT/US2009/068818, International Preliminary Report on Patentability, dated Jun. 21, 2011.
Japanese Patent Application No. 2015-525565, Notice of Reasons for Rejection, dated May 16, 2017.
Japanese Patent Application No. 2018-058524, Notice of Reasons for Rejection, dated Dec. 27, 2018.
Kaiser, Clinical research. Death prompts a review of gene therapy vector, *Science*, 317(5838):580 (2007).
Kaminsky and Ascano, p. 1-4 (2017).
Kaspar et al., Retrograde viral delivery of IGF-1 prolongs survival in a mouse ALS model, *Science*, 301(5634):839-42 (2003).
Katz et al., Preclinical research in Rett syndrome: setting the foundation for translational success, *Dis. Model Mech.*, 5(6):733-45 (2012).
Kempermann et al., Genetic influence on neurogenesis in the dentate gyrus of adult mice, *Proc. Natl. Acad. Sci. USA*, 94(19):10409-14 (1997).
Kim et al., Trendelenburg position with hip flexion as a rescue strategy to increase spinal anaesthetic level after spinal block, *Br. J. Anaesth.*, 98(3):396-400 (2007).
Klein et al., AAV8, 9, Rh10, Rh43 vector gene transfer in the rat brain: effects of serotype, promoter and purification method, *Mol. Ther.*, 16(1):89-96 (2008).

(56) References Cited

OTHER PUBLICATIONS

Koerber et al., Molecular Evolution of Adeno-associated Virus for Enhanced Glial Gene Delivery, *Molecular Therapy: the Journal of the American Society of Gene Therapy*, 17:2088-2095 (2009).
Kohan et al., Therapeutic approaches to the challenge of neuronal ceroid lipofuscinoses, *Curr. Pharm. Biotechnol.*, 12(6):867-83 (2011).
Kong et al., Impaired synaptic vesicle release and immaturity of neuromuscular junctions in spinal muscular atrophy mice, *J. Neurosci.*, 29(3):842-51 (2009).
Kosai et al., Rett syndome is reversible and treatable by MeCP2 gene therapy into the striatum in mice, *Molecular Ther.*, 11 (Suppl. 1):S24, Abstract 58 (May 2005).
Kota et al., Follistatin gene delivery enhances muscle growth and strength in nonhuman primates, *Sci. Transl. Med.*, 1:6-15 (2009).
Le et al., SMNDelta7, the major product of the centromeric survival motor neuron (SMN2) gene, extends survival in mice with spinal muscular atrophy and associates with full-length SMN, *Hum. Mol. Genet.*, 14(6):845-57 (2005).
Lioy et al., A role for glia in the progression of Rett's syndrome, *Nature*, 475:497-500 (2011).
Maguire et al., Directed evolution of adeno-associated virus for glioma cell transduction, *Journal of Neuro-Oncology*, 96:337-347.
McAllister et al., Mechanisms of glucose transport at the blood-brain barrier: an in vitro study, *Brain Res.*, 904(1):20-30 (2001).
McIlwain, "Chemical and enzymic make-up of the brain during development" In: McIlwain, Biochemistry and the Central Nervous System, London: Churchill Livingstone (1966).
Monani et al., A transgene carrying an A2G missense mutation in the SMN gene modulates phenotypic severity in mice with severe (type I) spinal muscular atrophy, *J. Cell Biol.*, 160(1):41-52 (2003).
Monani et al., The human centromeric survival motor neuron gene (SMN2) rescues embryonic lethality in Smn(-/-) mice and results in a mouse with spinal muscular atrophy, *Hum. Mol. Genet.*, 9(3):333-9 (2000).
Nagai et al., A transcriptional repressor MeCP2 causing Rett syndrome is expressed in embryonic non-neuronal cells and controls their growth, Brain Res., *Dev. Brain Res.*, 157(1):103-6 (2005).
Narver et al., Sustained improvement of spinal muscular atrophy mice treated with trichostatin A plus nutrition, *Ann. Neurol.*, 64(4):465-70 (2008).
Notice of Reasons for Rejection (English translation), Japanese patent application No. 2015/525565, dated May 16, 2017.
Oertle et al., Nogo-A inhibits neurite outgrowth and cell spreading with three discrete regions, *J. Neurosci.*, 23(13):5393-406 (2003).
Oprea et al., Plastin 3 is a protective modifier of autosomal recessive spinal muscular atrophy, *Science*, 320(5875):524-7 (2008).
Pardridge, Drug and gene targeting to the brain with molecular Trojan horses, *Nat. Rev. Drug Discov.*, 1(2):131-9 (2002).
Penta, Sulla colorazione vitale del sistema nervoso central negli animali neonati, *Riv. di Neurol.*, 5:62-80 (1932).
Perabo et al., Combinatorial engineering of a gene therapy vector: directed evolution of adeno-associated virus, *The Journal of Gene Medicine*, 8:155-162.
Ralph et al., Silencing mutant SOD1 using RNAi protects against neurodegeneration and extends survival in an ALS model, *Nat. Med.*, 11(4):429-33 (2005).
Rastegar et al., MECP2 isoform-specific vectors with regulated expression for Rett syndrome gene therapy, *PLoS One*, 4(8):e6810 (2009).
Reichenbach et al., pp. 19-35 In: Kettemann et al., Neuroglia, 2nd ed., New York: Oxford University Press (2004).
Risau et al., Development of the blood-brain barrier, *Trends Neurosci.*, 13(5):174-8 (1990).
Risau et al., Differentiation-dependent expression of proteins in brain endothelium during development of the blood-brain barrier, *Dev. Biol.*, 117(2):537-45 (1986).
Robinson et al., Morphological and functional reversal of phenotypes in a mouse model of Rett syndrome, *Brain*, 135(Pt. 9):2699-710 (2012).
Royo et al., Specific AAV serotypes stably transduce primary hippocampal and cortical cultures with high efficiency and low toxicity, *Brain Res.*, 1190:15-22 (2008).
Rubin et al., A cell culture model of the blood-brain barrier, *J. Cell Biol.*, 115(6):1725-35 (1991).
Saunders et al., On the progestational activity of 17alpha-ethynyl-17-hydroxy-5(10)-estren-3-one (norethynodrel), *Endocrinology*, 60(6):804-5 (1957).
Schlageter et al., Microvessel organization and structure in experimental brain tumors: microvessel populations with distinctive structural and functional properties, *Microvasc. Res.*, 58(3):312-28 (1999).
Setayesh et al., The Trendelenburg position increases the spread and accelerates the onset of epidural anesthesia for Cesarean section, *Can. J. Anaesth.*, 48(9):890-3 (Oct. 2001).
Siegel et al., Francis Crick's legacy for neuroscience: between the alpha and the Omega, *PLoS Biol.*, 2(12):e419 (2004).
Sinnett et al., Recent endeavors in MECP2 gene transfer for gene therapy of Rett syndrome, *Discov. Med.*, 24:153-9 (2017).
Skene et al., Neuronal MeCP2 is expressed at near histone-octamer levels and globally alters the chromatin state, *Mol. Cell*, 37(4):457-68 (2010).
Snyder et al., Comparison of adeno-associated viral vector serotypes for spinal cord and motor neuron gene delivery, *Hum. Gene. Ther.*, 22(9):1129-35 (2011).
Sobue et al., Induction of blood-brain barrier properties in immortalized bovine brain endothelial cells by astrocytic factors, *Neurosci. Res.*, 35(2):155-64 (1999).
Stern et al., Platelet lipoxygenase in spontaneously hypertensive rats, *Hypertension*, 27(5):1149-52 (1996).
Stewart et al., Interendothelial junctional changes underlie the developmental 'tightening' of the blood-brain barrier, *Brain Res.*, 429(2):271-81 (1987).
Turner et al., Administration of substances to laboratory animals: routes of administration and factors to consider, *J. Am. Assoc. Lab Anim. Sci.*, 50(5):600-13 (2011).
Verkman, Aquaporin water channels and endothelial cell function, *J. Anat.*, 200(6):617-27 (2002).
Virgintino et al., Immunolocalization of tight junction proteins in the adult and developing human brain, Histochem, *Cell Biol.*, 122(1):51-9 (2004).
Vorbrodt et al., Localization of alkaline phosphatase activity in endothelia of developing and mature mouse blood-brain barrier, *Dev. Neurosci.*, 8:1-13 (1986).
Wang et al., Decreased synaptic activity shifts the calcium dependence of release at the mammalian neuromuscular junction in vivo, *J. Neurosci.*, 24(47):10687-92 (2004).
Watson et al., Postnatal growth and morphological development of the brain: a species comparison, *Birth Defects Res. B Dev. Reprod. Toxicol.*, 77(5):471-84 (2006).
Wolburg et al., Tight junctions of the blood-brain barrier: development, composition and regulation, *Vascul. Pharmacol.*, 38(6):323-37 (2002).
Wolburg, pp. 77-107 In: Dermietzel et al., (eds.), Blood-Brain Interfaces—from Ontogeny to Artificial Barriers, Wiley-VCH (2006).
Wu et al., Single amino acid changes can influence titer, heparin binding, and tissue tropism in different adeno-associated virus serotypes, *Journal of Virology*, 80:11393-11397.
Yamanaka et al., Astrocytes as determinants of disease progression in inherited amyotrophic lateral sclerosis, *Nat. Neurosci.*, 11(3):251-3 (2008).
Carter, "Adeno-Associated Virus Vectors in Clinical Trials", Human Gene Therapy, 16:541-550 (2005).
Dalkara et al. "In Vivo-Directed Evolution of a New Adeno-Associated Virus for Therapeutic Outer Retinal Gene Deliver from the Vitreous," Science Translational Medicine, 5(189):1-11 (2013).
Edelstein et al., "Gene therapy clinical trials worldwide 1989-2004—an overview", The Journal of Gene Medicine, 6:597-602 (2004).
Final Rejection issued in U.S. Appl. No. 16/159,986 dated Mar. 4, 2021.
Maguire et al., "Gene Therapy for the Nervous System: Challenges and New Strategies," Neurotherapeutics, 11:817-839 (2004).

(56) References Cited

OTHER PUBLICATIONS

Ruzo et al., "AAV-mediated sulphamidase expression in liver or skeletal muscle prevents development of somatic alterations in MPS IIIA mice," Molecular Therapy, 16(1):S197 (2008).

Storek et al., "Sensory neuron targeting by self-complementary AAV8 via lumbar puncture for chronic pain", PNAS, 105(3):1055-1060 (2008).

Towne et al., "Recombinant adeno-associated virus serotype 6 (rAAV2/6)-mediated gene transfer to nociceptive neurons through different routes of delivery", Molecular Pain, 5(52):1-17 (2009).

NCBI accession No. AY414351, *Homo sapiens* SGSH gene, Virtual Transcript, partial sequence, genomic survey sequence, pp. 1-2 (Year: 2003).

Sequence alignment of NCBI accession No. AY414351 vs SEQ ID No. 3, pp. 1-3 (Year: 2003).

Yogalingam et al., "Molecular Genetics of Mucopolysaccharidosis Type IIIA and IIIB: Diagnostic, Clinical, and Biological Implications," *Human Mutation*, 18:264-81 (2001).

Grimm et al., Progress in Adeno-Associated Virus Type 2 Vector Production: Promises and Prospects for Clinical Use, *Human Gene Therapy* 10:2445-50 (1999).

Heon-Roberts et al., Molecular ases of Neurodegeneration and Cognitive Decline, the Major Burden of Sanfilippo Disease, *Journal of Clinical Medicine* 9(344):1-25 (2020).

Fu et al., Optimization of AAV Stereotype and Promoter for Increased Distribution of Espression in Both Somatic and Central Nervous Systems of Mice, *Molecular Therapy* (854) 11(S1):S332 (2005).

\* cited by examiner a.

b.

SEQUENCE LISTING

```
<160> NUMBER OF SEQ ID NOS: 11

<210> SEQ ID NO 1
<211> LENGTH: 2232
<212> TYPE: DNA
<213> ORGANISM: Homo sapiens
<300> PUBLICATION INFORMATION:
<308> DATABASE ACCESSION NUMBER: GenBank / U43573.1
<309> DATABASE ENTRY DATE: 1996-06-11
<313> RELEVANT RESIDUES IN SEQ ID NO: (1)..(2232)

<400> SEQUENCE: 1
atggaggcgg tggcggtggc cgcggcggtg ggggtccttc tcctggccgg ggccggggc      60 gcggcaggcg acgaggcccg ggaggcggcg gccgtgcggg cgctcgtggc ccggctgctg     120
gggccaggcc ccgcggccga cttctccgtg tcggtggagc gcgctctggc tgccaagccg     180
ggcttggaca cctacagcct gggcggcggc ggcgcggcgc gcgtgcgggt gcgcggctcc     240
acgggcgtgg cggccgccgc ggggctgcac cgctacctgc gcgacttctg tggctgccac     300
gtggcctggt ccggctctca gctgcgcctg ccgcggccac tgccagccgt gccggggggag     360 ctgaccgagg ccacgcccaa caggtaccgc tattaccaga atgtgtgcac gcaaagctac     420
tccttcgtgt ggtgggactg ggcccgctgg gagcgagaga tagactggat ggcgctgaat     480
ggcatcaacc tggcactggc ctggagcggc caggaggcca tctggcagcg ggtgtacctg     540
gccttgggcc tgacccaggc agagatcaat gagttctttta ctggtcctgc cttcctggcc     600 tggggggcgaa tgggcaacct gcacacctgg gatgccccc tgccccccctc ctggcacatc     660 aagcagcttt acctgcagca ccgggtcctg gaccagatgc gctccttcgg catgacccca     720
```

```
gtgctgcctg cattcgcggg gcatgttccc gaggctgtca ccagggtgtt ccctcaggtc      780
aatgtcacga agatgggcag ttggggccac tttaactgtt cctactcctg ctccttcctt      840
ctggctccgg aagacccat  attcccatc  atcgggagcc tcttcctgcg agagctgatc      900
aaagagtttg gcacagacca catctatggg gccgacactt tcaatgagat gcagccacct      960
tcctcagagc cctcctacct tgccgcagcc accactgccg tctatgaggc catgactgca     1020
gtggatactg aggctgtgtg gctgctccaa ggctggctct tccagcacca gccgcagttc     1080
tgggggcccg cccagatcag ggctgtgctg ggagctgtgc ccgtggccg  cctcctggtt     1140 ctggacctgt ttgctgagag ccagcctgtg tatacccgca ctgcctcctt ccagggccag     1200
cccttcatct ggtgcatgct gcacaacttt ggggaaacc  atggtctttt ggagcccta     1260 gaggctgtga acgaggccc  agaagctgcc cgcctcttcc ccaactccac catggtaggc     1320
acgggcatgg ccccgaggg  catcagccag aacgaagtgg tctattccct catggctgag     1380
ctgggctggc gaaaggaccc agtgccagat ttggcagcct gggtgaccag ctttgccgcc     1440
cggcggtatg gggtctccca cccggacgca ggggcagcgt ggaggctact gctccggagt     1500
gtgtacaact gctccgggga ggcctgcagg ggccacaatc gtagcccgct ggtcaggcgg     1560
ccgtccctac agatgaatac cagcatctgg tacaaccgat ctgatgtgtt tgaggcctgg     1620
cggctgctgc tcacatctgc tccctccctg gccaccagcc ccgccttccg ctacgacctg     1680
ctggacctca ctcggcaggc agtgcaggag ctggtcagct tgtactatga ggaggcaaga     1740
agcgcctacc tgagcaagga gctggcctcc ctgttgaggg ctggaggcgt cctggcctat     1800
gagctgctgc cggcactgga cgaggtgctg gctagtgaca gccgcttctt gctgggcagc     1860
tggctagagc aggcccgagc agcggcagtc agtgaggccg aggccgattt ctacgagcag     1920
aacagccgct accagctgac cttgtggggg ccagaaggca acatcctgga ctatgccaac     1980
aagcagctgg cggggttggt ggccaactac tacaccctc  gctggcggct tttcctggag     2040
gcgctggttg acagtgtggc ccagggcatc cctttccaac agcaccagtt tgacaaaaat     2100
gtcttccaac tggagcaggc cttcgttctc agcaagcaga ggtaccccag ccagccgcga     2160
ggagacactg tggacctggc caagaagatc ttcctcaaat attacccgg  ctgggtggcc     2220 ggctcttggt ga                                                         2232
```

<210> SEQ ID NO 2
<211> LENGTH: 743
<212> TYPE: PRT
<213> ORGANISM: Homo sapiens
<300> PUBLICATION INFORMATION:
<308> DATABASE ACCESSION NUMBER: GenBank / U43573.1
<309> DATABASE ENTRY DATE: 1996-06-11
<313> RELEVANT RESIDUES IN SEQ ID NO: (1)..(743)

<400> SEQUENCE: 2

```
Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80
```

-continued

```
Thr Gly Val Ala Ala Ala Gly Leu His Arg Tyr Leu Arg Asp Phe
                85                  90                  95
Cys Gly Cys His Val Ala Trp Ser Gly Ser Gln Leu Arg Leu Pro Arg
            100                 105                 110
Pro Leu Pro Ala Val Pro Gly Glu Leu Thr Glu Ala Thr Pro Asn Arg
            115                 120                 125
Tyr Arg Tyr Tyr Gln Asn Val Cys Thr Gln Ser Tyr Ser Phe Val Trp
        130                 135                 140
Trp Asp Trp Ala Arg Trp Glu Arg Glu Ile Asp Trp Met Ala Leu Asn
145                 150                 155                 160
Gly Ile Asn Leu Ala Leu Ala Trp Ser Gly Gln Glu Ala Ile Trp Gln
                165                 170                 175
Arg Val Tyr Leu Ala Leu Gly Leu Thr Gln Ala Glu Ile Asn Glu Phe
                180                 185                 190
Phe Thr Gly Pro Ala Phe Leu Ala Trp Gly Arg Met Gly Asn Leu His
            195                 200                 205
Thr Trp Asp Gly Pro Leu Pro Pro Ser Trp His Ile Lys Gln Leu Tyr
        210                 215                 220
Leu Gln His Arg Val Leu Asp Gln Met Arg Ser Phe Gly Met Thr Pro
225                 230                 235                 240
Val Leu Pro Ala Phe Ala Gly His Val Pro Glu Ala Val Thr Arg Val
                245                 250                 255
Phe Pro Gln Val Asn Val Thr Lys Met Gly Ser Trp Gly His Phe Asn
            260                 265                 270
Cys Ser Tyr Ser Cys Ser Phe Leu Leu Ala Pro Glu Asp Pro Ile Phe
        275                 280                 285
Pro Ile Ile Gly Ser Leu Phe Leu Arg Glu Leu Ile Lys Glu Phe Gly
        290                 295                 300
Thr Asp His Ile Tyr Gly Ala Asp Thr Phe Asn Glu Met Gln Pro Pro
305                 310                 315                 320
Ser Ser Glu Pro Ser Tyr Leu Ala Ala Ala Thr Thr Ala Val Tyr Glu
                325                 330                 335
Ala Met Thr Ala Val Asp Thr Glu Ala Val Trp Leu Leu Gln Gly Trp
            340                 345                 350
Leu Phe Gln His Gln Pro Gln Phe Trp Gly Pro Ala Gln Ile Arg Ala
        355                 360                 365
Val Leu Gly Ala Val Pro Arg Gly Arg Leu Leu Val Leu Asp Leu Phe
        370                 375                 380
Ala Glu Ser Gln Pro Val Tyr Thr Arg Thr Ala Ser Phe Gln Gly Gln
385                 390                 395                 400
Pro Phe Ile Trp Cys Met Leu His Asn Phe Gly Gly Asn His Gly Leu
                405                 410                 415
Phe Gly Ala Leu Glu Ala Val Asn Gly Gly Pro Glu Ala Ala Arg Leu
            420                 425                 430
Phe Pro Asn Ser Thr Met Val Gly Thr Gly Met Ala Pro Glu Gly Ile
        435                 440                 445
Ser Gln Asn Glu Val Val Tyr Ser Leu Met Ala Glu Leu Gly Trp Arg
        450                 455                 460
Lys Asp Pro Val Pro Asp Leu Ala Ala Trp Val Thr Ser Phe Ala Ala
465                 470                 475                 480
Arg Arg Tyr Gly Val Ser His Pro Asp Ala Gly Ala Ala Trp Arg Leu
                485                 490                 495
```

| Leu | Leu | Arg | Ser | Val | Tyr | Asn | Cys | Ser | Gly | Glu | Ala | Cys | Arg | Gly | His |
|---|---|---|---|---|---|---|---|---|---|---|---|---|---|---|---|
| | | | 500 | | | | | 505 | | | | | 510 | | |

Asn Arg Ser Pro Leu Val Arg Arg Pro Ser Leu Gln Met Asn Thr Ser
    515                   520                 525

Ile Trp Tyr Asn Arg Ser Asp Val Phe Glu Ala Trp Arg Leu Leu Leu
530                     535                 540

Thr Ser Ala Pro Ser Leu Ala Thr Ser Pro Ala Phe Arg Tyr Asp Leu
545              550               555               560

Leu Asp Leu Thr Arg Gln Ala Val Gln Glu Leu Val Ser Leu Tyr Tyr
              565               570               575

Glu Glu Ala Arg Ser Ala Tyr Leu Ser Lys Glu Leu Ala Ser Leu Leu
        580                 585               590

Arg Ala Gly Gly Val Leu Ala Tyr Glu Leu Leu Pro Ala Leu Asp Glu
        595                 600               605

Val Leu Ala Ser Asp Ser Arg Phe Leu Leu Gly Ser Trp Leu Glu Gln
610                     615                 620

Ala Arg Ala Ala Ala Val Ser Glu Ala Glu Ala Asp Phe Tyr Glu Gln
625              630               635               640

Asn Ser Arg Tyr Gln Leu Thr Leu Trp Gly Pro Glu Gly Asn Ile Leu
              645               650               655

Asp Tyr Ala Asn Lys Gln Leu Ala Gly Leu Val Ala Asn Tyr Tyr Thr
        660                 665               670

Pro Arg Trp Arg Leu Phe Leu Glu Ala Leu Val Asp Ser Val Ala Gln
              675               680               685

Gly Ile Pro Phe Gln Gln His Gln Phe Asp Lys Asn Val Phe Gln Leu
        690                 695               700

Glu Gln Ala Phe Val Leu Ser Lys Gln Arg Tyr Pro Ser Gln Pro Arg
705                     710               715               720

Gly Asp Thr Val Asp Leu Ala Lys Lys Ile Phe Leu Lys Tyr Tyr Pro
              725               730               735

Gly Trp Val Ala Gly Ser Trp
        740

<210> SEQ ID NO 3
<211> LENGTH: 1509
<212> TYPE: DNA
<213> ORGANISM: Homo sapiens
<300> PUBLICATION INFORMATION:
<308> DATABASE ACCESSION NUMBER: GenBank / U30894.1
<309> DATABASE ENTRY DATE: 1996-02-02
<313> RELEVANT RESIDUES IN SEQ ID NO: (1)..(1509)

<400> SEQUENCE: 3

```
atgagctgcc ccgtgcccgc ctgctgcgcg ctgctgctag tcctggggct ctgccgggcg      60
cgtccccgga acgcactgct gctcctcgcg gatgacggag gctttgagag tggcgcgtac     120
aacaacagcg ccatcgccac cccgcacctg gacgccttgg cccgccgcag cctcctcttt     180
cgcaatgcct tcacctcggt cagcagctgc tctcccagcc gcgccagcct cctcactggc     240 ctgcccagc atcagaatgg gatgtacggg ctgcaccagg acgtgcacca cttcaactcc     300
ttcgacaagg tgcggagcct gccgctgctg ctcagccaag ctggtgtgcg cacaggcatc     360
atcgggaaga agcacgtggg gccggagacc gtgtacccgt tgactttgc gtacacggag     420 gagaatggct ccgtcctcca ggtggggcgg aacatcacta gaattaagct gctcgtccgg     480
aaattcctgc agactcagga tgaccggcct tcttcctct acgtcgcctt ccacgacccc     540
caccgctgtg ggcactccca gccccagtac ggaaccttct gtgagaagtt tggcaacgga     600
```

-continued

```
gagagcggca tgggtcgtat cccagactgg accccccagg cctacgaccc actggacgtg    660
ctggtgcctt acttcgtccc caacaccccg gcagcccgag ccgacctggc cgctcagtac    720
accaccgtcg gccgcatgga ccaaggagtt ggactggtgc tccaggagct gcgtgacgcc    780
ggtgtcctga cgacacact  ggtgatcttc acgtccgaca acgggatccc cttccccagc    840
ggcaggacca acctgtactg gccgggcact gctgaaccct tactggtgtc atccccggag    900
cacccaaaac gctggggcca agtcagcgag gcctacgtga gcctcctaga cctcacgccc    960
accatcttgg attggttctc gatcccgtac cccagctacg ccatctttgg ctcgaagacc   1020
atccacctca ctggccggtc cctcctgccg gcgctggagg ccgagcccct ctgggccacc   1080
gtctttggca gccagagcca ccacgaggtc accatgtcct accccatgcg ctccgtgcag   1140
caccggcact ccgcctcgt  gcacaacctc aacttcaaga tgccctttcc catcgaccag   1200
gacttctacg tctcacccac cttccaggac ctcctgaacc gcaccacagc tggtcagccc   1260
acgggctggt acaaggacct ccgtcattac tactaccggg cgcgctggga gctctacgac   1320
cggagccggg acccccacga gacccagaac ctggccaccg accgcgcctt tgctcagctt   1380
ctggagatgc ttcgggacca gctggccaag tggcagtggg agaccacga  ccctgggtg    1440 tgcgcccccg acggcgtcct ggaggagaag ctctctcccc agtgccagcc cctccacaat   1500
gagctgtga                                                           1509
```

```
<210> SEQ ID NO 4
<211> LENGTH: 502
<212> TYPE: PRT
<213> ORGANISM: Homo sapiens
<300> PUBLICATION INFORMATION:
<308> DATABASE ACCESSION NUMBER: GenBank / U30894.1
<309> DATABASE ENTRY DATE: 1996-02-02
<313> RELEVANT RESIDUES IN SEQ ID NO: (1)..(502)

<400> SEQUENCE: 4

Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
                20                  25                  30

Gly Gly Phe Glu Ser Gly Ala Tyr Asn Asn Ser Ala Ile Ala Thr Pro
            35                  40                  45

His Leu Asp Ala Leu Ala Arg Arg Ser Leu Leu Phe Arg Asn Ala Phe
        50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
                100                 105                 110

Gln Ala Gly Val Arg Thr Gly Ile Ile Gly Lys Lys His Val Gly Pro
            115                 120                 125

Glu Thr Val Tyr Pro Phe Asp Phe Ala Tyr Thr Glu Glu Asn Gly Ser
        130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
```

```
            180                 185                 190
Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500

<210> SEQ ID NO 5
<211> LENGTH: 3878
<212> TYPE: DNA
<213> ORGANISM: Homo sapiens

<400> SEQUENCE: 5
gggggggggg gggggggtt ggccactccc tctctgcgcg ctcgctcgct cactgaggcc      60
gggcgaccaa aggtcgcccg acgcccgggc tttgcccggg cggcctcagt gagcgagcga    120
gcgcgcagag agggagtggc caactccatc actaggggtt cctagatctg aattcggtac    180
ccgttacata acttacggta atggcccgc ctggctgacc gcccaacgac ccccgcccat    240
tgacgtcaat aatgacgtat gttcccatag taacgccaat agggactttc cattgacgtc    300
```

-continued

```
aatgggtgga gtatttacgg taaactgccc acttggcagt acatcaagtg tatcatatgc   360
caagtacgcc ccctattgac gtcaatgacg gtaaatggcc cgcctggcat tatgcccagt   420
acatgacctt atgggacttt cctacttggc agtacatcta cgtattagtc atcgctatta   480
ccatggtgat gcggttttgg cagtacatca atgggcgtgg atagcggttt gactcacggg   540
gatttccaag tctccacccc attgacgtca atgggagttt gttttggcac caaaatcaac   600
gggactttcc aaaatgtcgt aacaactccg cccattgac gcaaatgggc ggtaggcgtg   660
tacggtggga ggtctatata agcagagctc gtttagtgaa ccgtcagatc gcctggagac   720
gccatccacg ctgttttgac ctccatagaa gacaccggga ccgatccagc ctccggactc   780
tagaggatcc ggtactcgag gaactgaaaa accagaaagt taactggtaa gtttagtctt   840
tttgtctttt atttcaggtc ccggatccgg tggtggtgca aatcaaagaa ctgctcctca   900
gtggatgttg cctttacttc taggcctgta cggaagtgtt acttctgctc taaaagctgc   960
ggaattgtac ccgcggcccg ggatccaccg gaattcagac catggaggcg gtggcggtgg  1020
ccgcggcggt gggggtcctt ctcctggccg gggccggggg cgcggcaggc gacgaggccc  1080
gggaggcggc ggccgtgcgg gcgctcgtgg cccggctgct ggggccaggc cccgcggccg  1140
acttctccgt gtcggtggag cgcgctctgg ctgccaagcc gggcttggac acctacagcc  1200
tgggcggcgg cggcgcggcg cgcgtgcggg tgcgcggctc cacggcgtg gcggccgccg  1260
cggggctgca ccgctacctg cgcgacttct gtggctgcca cgtggcctgg tccggctctc  1320
agctgcgcct gccgcggcca ctgccagccg tgccggggga gctgaccgag gccacgccca  1380
acaggtaccg ctattaccag aatgtgtgca cgcaaagcta ctccttcgtg tggtgggact  1440
gggcccgctg ggagcgagag atagactgga tggcgctgaa tggcatcaac ctggcactgg  1500
cctggagcgg ccaggaggcc atctggcagc gggtgtacct ggccttgggc ctgacccagg  1560
cagagatcaa tgagttcttt actggtcctg ccttcctggc ctggggcga atgggcaacc  1620
tgcacacctg ggatggcccc ctgccccct cctggcacat caagcagctt tacctgcagc  1680
accgggtcct ggaccagatg cgctccttcg gcatgacccc agtgctgcct gcattcgcgg  1740
ggcatgttcc cgaggctgtc accagggtgt cccctcaggt caatgtcacg aagatgggca  1800
gttggggcca cttaactgt tcctactcct gctccttcct tctggctccg aagaccca  1860
tattccccat catcgggagc ctcttcctgc gagagctgat caaagagttt ggcacagacc  1920
acatctatgg ggccgacact ttcaatgaga tgcagccacc ttcctcagag ccctcctacc  1980
ttgccgcagc caccactgcc gtctatgagg ccatgactgc agtggatact gaggctgtgt  2040
ggctgctcca aggctggctc ttccagcacc agccgcagtt ctggggcc gcccagatca  2100
gggctgtgct gggagctgtg cccgtggcc gcctcctggt tctggacctg tttgctgaga  2160
gccagcctgt gtatacccgc actgcctcct tccagggcca gcccttcatc tggtgcatgc  2220
tgcacaactt tggggaaac catggtcttt tggagcccct agaggctgtg aacgaggcc  2280
cagaagctgc ccgcctcttc cccaactcca ccatggtagg cacgggcatg gcccccgagg  2340
gcatcagcca gaacgaagtg gtctattccc tcatggctga gctgggctgg cgaaaggacc  2400
cagtgccaga tttggcagcc tgggtgacca gctttgccgc ccggcggtat ggggtctccc  2460
acccggacgc aggggcagcg tggaggctac tgctccggag tgtgtacaac tgctccgggg  2520
aggcctgcag gggccacaat cgtagcccgc tggtcaggcg gccgtcccta cagatgaata  2580
ccagcatctg gtacaaccga tctgatgtgt ttgaggcctg gcggctgctg ctcacatctg  2640
```

```
ctccctccct ggccaccagc cccgccttcc gctacgacct gctggacctc actcggcagg    2700
cagtgcagga gctggtcagc ttgtactatg aggaggcaag aagcgcctac ctgagcaagg    2760
agctggcctc cctgttgagg gctggaggcg tcctggccta tgagctgctg ccggcactgg    2820
acgaggtgct ggctagtgac agccgcttct tgctgggcag ctggctagag caggcccgag    2880
cagcggcagt cagtgaggcc gaggccgatt tctacgagca gaacagccgc taccagctga    2940
ccttgtgggg gccagaaggc aacatcctgg actatgccaa caagcagctg gcggggttgg    3000
tggccaacta ctacacccct cgctggcggc ttttcctgga ggcgctggtt gacagtgtgg    3060
cccagggcat ccctttccaa cagcaccagt ttgacaaaaa tgtcttccaa ctggagcagg    3120
ccttcgttct cagcaagcag aggtaccccca gccagccgcg aggagacact gtggacctgg    3180
ccaagaagat cttcctcaaa tattaccccg gctgggtggc cggctcttgg tgatagattc    3240
gccaccactg ggccttgttt tccgctaatt ccagggcaga ttccagggcc cagagctgga    3300
cagacatcac aggataaccc aggcctggga ggaggcccca cggcctgctg gtggggtctg    3360 acctggggg attggaggga aatgacctgc cctccaccac cacccaaagt gtgggattgg    3420
taccgagctc ggatccacta gtcccgggcc atcacactgg gaattggccg cgtcgactag    3480
agctcgctga tcagcctcga ctgtgccttc tagttgccag ccatctgttg tttgcccctc    3540
ccccgtgcct tccttgaccc tggaaggtgc cactcccact gtcctttcct aataaaatga    3600
ggaaattgca tcgcattgtc tgagtaggtg tcattctatt ctgggggtg gggtggggca    3660 ggacagcaag ggggaggatt gggaagacaa tagcaggcat gctggggaga gatctaggaa    3720
cccctagtga tggagttggc cactccctct ctgcgcgctc gctcgctcac tgaggccgcc    3780
cgggcaaagc ccgggcgtcg gcgacccttt ggtcgcccgg cctcagtgag cgagcgagcg    3840
cgcagagagg gagtggccaa ccccccccc cccccccc                             3878
```

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
ggcagtacat caagtgtatc                                                 20

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
accaatggta atagcgatga c                                               21

<210> SEQ ID NO 8
<211> LENGTH: 20
<212> TYPE: DNA
<213> ORGANISM: Artificial Sequence
<220> FEATURE:
<223> OTHER INFORMATION: Synthetic probe

<400> SEQUENCE: 8
aatgacggta aatggcccgc                                                 20

```
<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
gtcatcacta ttggcaacga                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ctcaggagtt ttgtcacctt                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic probe

<400> SEQUENCE: 11
ttccgatgcc ctgaggctct                                              20
```

US 11,590,210 B2

METHODS FOR DELIVERY OF POLYNUCLEOTIDES BY ADENO-ASSOCIATED VIRUS FOR LYSOSOMAL STORAGE DISORDERS

This application is a continuation of U.S. patent application Ser. No. 13/491,326, filed Jun. 7, 2012, which claims the benefit of the filing date of U.S. Provisional Patent Application No. 61/494,635 filed Jun. 8, 2011, which is incorporated by reference herein in its entirety.

FIELD OF THE INVENTION

The present invention relates to methods and materials useful for systemically delivering polynucleotides across the blood brain barrier using adeno-associated virus as a vector. For example, the present invention relates to methods and materials useful for systemically delivering α-N-acetylglucosamidinase polynucleotides to the central and peripheral nervous systems, as well as the somatic system. Use of these methods and materials is indicated, for example, for treatment of the lysosomal storage disorder mucopolysaccharidosis IIIB. As another example, the present invention relates to methods and materials useful for systemically delivering N-sulphoglucosamine sulfphohydrolase polynucleotides to the central and peripheral nervous systems, as well as the somatic system. Use of this second type of methods and materials is indicated, for example, for treatment of the lysosomal storage disorder mucopolysaccharidosis IIIA.

INCORPORATION BY REFERENCE OF THE SEQUENCE LISTING

This application contains, as a separate part of disclosure, a Sequence Listing in computer-readable form (46031A_SeqListing.txt; 22,737 byte ASCII text file, created Jun. 7, 2012) which is incorporated by reference herein in its entirety.

BACKGROUND

Mucopolysaccharidosis (MPS) IIIB is a devastating lysosomal storage disease (LSD) caused by autosomal recessive defects in the gene coding a lysosomal enzyme, α-N-Acetylglucosaminidase (NAGLU). The lack of NAGLU activity disrupts the stepwise degradation of a class of biologically important glycosaminoglycan (GAG), leading to the accumulation of heparan sulfate oligosaccharides in lysosomes in cells of most tissues. Cells throughout the CNS are particularly affected, resulting in complex secondary neuropathology. MPS IIIB infants appear normal at birth, but develop progressive neurological manifestations that lead to premature death. Somatic manifestations of MPS IIIB occur in all patients, and involve virtually all organs, although they are mild relative to other forms of MPS, such as MPS I, II and VII.

MPS IIIA is a related LSD caused by autosomal recessive defects in the gene encoding a lysosomal enzyme, N-sulphoglucosamine sulphohydrolase (SGSH). The lack of SGSH activity also disrupts the stepwise degradation of a class of biologically important GAG, leading to the accumulation of heparin sulfate oligosaccharides in lysosomes in cells of most tissues.

No treatment is currently available for MPS IIIB or IIIA. For all of the MPS disorders, therapies have historically been limited to supportive care and management of complications. MPS IIIB is not amenable to either hematopoietic stem cell transplantation or recombinant enzyme replacement therapy. These have instead been used to treat mostly somatic disorders in patients with MPS I, II and IV. This is because the neuropathology of MPS IIIB is global and the blood brain barrier (BBB) precludes effective central nervous system (CNS) access.

For the majority of CNS diseases, effective treatments are rare since the CNS is located in a well protected environment and isolated by a highly defined anatomical/functional barrier. The BBB is completely formed at birth in humans. In general, the BBB protects the CNS by selectively regulating the transport of molecules/agents from the blood circulation into the CNS or vice versa. Likewise, it prevents potential therapeutics from entering the CNS. The BBB remains the most critical challenge to developing therapies for CNS diseases, especially global CNS disorders.

It is contemplated herein that gene therapy has potential for treating LSDs because the secretion of lysosomal enzymes, including NAGLU and SGSH, leads to bystander effects thus reducing the demand for gene transfer efficiency. The adeno-associated virus (AAV) vector system is one system with demonstrated therapeutic effect in a great variety of disease models. To date, no known pathogenesis has been linked to AAV in humans. Recombinant AAV (rAAV) vectors based on AAV serotype 2 (AAV2) have been used in numerous studies for neurological diseases, transducing both neuronal and non-neuronal cells in the CNS with demonstrated therapeutic benefits in treating MPS and other LSDs in animals and in patients with Parkinson's and Batten's disease. In the majority of rAAV-CNS gene therapy studies in LSDs, vectors were delivered by direct intracranial injection, which has limited potential for treating global CNS diseases. See, Sands et al., *Acta Paediatr. Suppl.*, 97: 22-27 (2008); Fu et al., *Mol. Ther.*, 5: 42-49 (2002); Cressant et al., *J. Neurosci.*, 24: 10229-10239 (2004); Fraldi et al., *Hum. Mol. Genet.*, 16: 2693-2702 (2007); Worgall et al., *Hum. Gen. Ther.*, 19: 563-574 (2008) and Heldermon et al. *Mol. Ther.*, 18: 873-880 (2010). To overcome these obstacles, more efficient delivery approaches have been developed with broad or global transduction, and functional benefits for the neurological disease in adult MPS TIM mice. An intracisternal injection of rAAV2-hNAGLU vector in adult MPS IIIB mice, following mannitol pretreatment, led to deep periventricular transduction and clinical benefits. See Fu et al., *J. Gene Med.*, 12: 624-633 (2010). Intravenous (IV) rAAV injection into neonatal MPS I, MPS VII and MPS IIIB mice led to long-term correction of lysosomal storage in both somatic and CNS tissues. See, Sands et al., *Lab. Anim. Sci.*, 49: 328-330 (1999); Hartung et al., *Mol. Ther.*, 9: 866-875 (2004) and Heldermon et al., supra. However, the BBB may still be permeable in neonatal mice while closed at birth in humans. Previously, in adult MPS IIIB mice, pretreatment with an N infusion of mannitol transiently disrupting the BBB facilitated the CNS entry of IV-delivered rAAV2, resulting in diffuse global CNS transduction and neurological correction. See, McCarty et al., *Gene Ther.*, 16: 1340-1352 (2009).

Recombinant AAV9 vectors encoding the sulfamidase enzyme have been administered to MPSIIIA mice as reported in Ruzo et al., *XVIII Annual Congress of the European Society of Gene and Cell Therapy:* 1389 (Abstract Or 96) (October 2010) and Ruzo et al., *Mol. Therap.*, 20(2): 254-266 (2012).

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol,* 45: 555-564 (1983) as corrected by Ruffing et al., *J Gen Virol,* 75: 3385-3392 (1994). Cis-acting sequences directing viral DNA replication, encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology,* 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus, making cold preservation of AAV less critical. AAV may even be lyophilized. Finally, AAV-infected cells are not resistant to superinfection.

Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11. AAV9 is described in U.S. Pat. No. 7,198,951 and in Gao et al., *J. Virol.,* 78: 6381-6388 (2004). Advances in the delivery of AAV6 and AAV8 have made possible the transduction by these serotypes of skeletal and cardiac muscle following simple systemic intravenous or intraperitoneal injections. See, Pacak et al., *Circ. Res.,* 99(4): 3-9 (1006) and Wang et al., *Nature Biotech.,* 23(3): 321-328 (2005). The use of some serotypes of AAV to target cell types within the central nervous system, though, has required surgical intraparenchymal injection. See, Kaplitt et al., *Lancet* 369: 2097-2105 (2007); Marks et al., *Lancet Neurol* 7: 400-408 (2008); and Worgall et al., *Hum Gene Ther* (2008).

There remains a need in the art for products and methods for treating lysosomal storage disorders such as MPS IIIB and MPS IIIA.

SUMMARY

The present invention provides methods and materials useful for systemically delivering polynucleotides such as NAGLU polynucleotides or SGSH polynucleotides across the BBB.

According to the invention, gene delivery is achieved by utilizing, for example, AAV serotype 9 (AAV9). See, Foust et al., *Nature Biotechnology,* 27: 59-65 (2009); Duque et al., *Mol. Ther.* 17: 1187-1196 (2009); and Zincarelli et al., *Mol. Ther.,* 16: 1073-1080 (2008). Vectors based on this serotype or functionally-related serotypes are able to cross the BBB unaided in neonate and adult animals. An added benefit to using AAV9 vectors is that pre-existing immunity is less common than for AAV2 serotype. The use of rh74 serotype AAV vectors among others is also contemplated by the invention.

In one aspect, the invention provides a method of delivering a NAGLU polynucleotide across the BBB comprising systemically administering a rAAV9 with a genome including the polynucleotide to a patient. In some embodiments the rAAV9 genome is a single-stranded genome.

More specifically, the present invention provides methods and materials useful for systemically delivering NAGLU polynucleotides across the blood brain barrier to the central and peripheral nervous system. In some embodiments, a method is provided of delivering a polynucleotide to the central nervous system comprising systemically administering a rAAV9 with a single-stranded genome including the genome to a patient. In some embodiments, a method of delivering a NAGLU polynucleotide to the peripheral nervous system comprising systemically administering a rAAV9 with a single-stranded genome including the polynucleotide to a patient is provided.

Even more specifically, in some embodiments, the NAGLU polynucleotide is delivered to brain. In some embodiments, the polynucleotide is delivered to the spinal cord. In some embodiments, the NAGLU polynucleotide is delivered to a lower motor neuron. In some embodiments, the polynucleotide is delivered to nerve and glial cells. In some embodiments, the glial cell is a microglial cell, an oligodendrocyte or an astrocyte. In some, embodiments, the rAAV9 is used to deliver a NAGLU polynucleotide to a Schwann cell.

Use of the NAGLU methods and materials is indicated, for example, for treating Sanfilippo syndrome Type B/MPS IIIB.

In another aspect, the invention provides a method of delivering an SGSH polynucleotide across the BBB comprising systemically administering a rAAV9 with a genome including the polynucleotide to a patient. In some embodiments, the rAAV9 genome is a self-complementary genome. In some embodiments the rAAV9 genome is a single-stranded genome.

More specifically, the present invention provides methods and materials useful for systemically delivering SGSH polynucleotides across the blood brain barrier to the central and peripheral nervous system. In some embodiments, a method is provided of delivering a polynucleotide to the central nervous system comprising systemically administering a rAAV9 with a self-complementary genome including the genome to a patient. In some embodiments, a method of delivering a SGSH polynucleotide to the peripheral nervous system comprising systemically administering a rAAV9 with a self-complementary genome including the polynucleotide to a patient is provided.

Even more specifically, in some embodiments, the SGSH polynucleotide is delivered to brain. In some embodiments, the polynucleotide is delivered to the spinal cord. In some embodiments, the SGSH polynucleotide is delivered to a lower motor neuron. In some embodiments, the polynucleotides is delivered to nerve and glial cells. In some embodiments, the glial cell is a microglial cell, an oligodendrocyte or an astrocyte. In some, embodiments, the rAAV9 is used to deliver a SGSH polynucleotide to a Schwann cell.

Use of the SGSH methods and materials is indicated, for example, for treating MPS IIIA.

In yet another aspect, administration of the rAAV9 encoding a NAGLU or SGSH polypeptide is preceded by administration of mannitol.

In still another aspect, the invention provides rAAV genomes comprising one or more AAV ITRs flanking a polynucleotide encoding a NAGLU. The NAGLU polynucleotide is operatively linked to transcriptional control DNAs, specifically promoter DNA and polyadenylation signal sequence DNA that are functional in target cells to form a gene cassette. The gene cassette may also include intron sequences to facilitate processing of an RNA transcript when expressed in mammalian cells.

In a further aspect, the invention provides rAAV genomes comprising one or more AAV ITRs flanking a polynucleotide encoding an SGSH. The SGSH polynucleotide is operatively linked to transcriptional control DNAs, specifically promoter DNA and polyadenylation signal sequence DNA that are functional in target cells to form a gene cassette. The gene cassette may also include intron sequences to facilitate processing of an RNA transcript when expressed in mammalian cells.

The rAAV genomes of the invention lack AAV rep and cap DNA. AAV DNA in the rAAV genomes (e.g., ITRs) may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC_001401 and Srivastava et al., *J. Virol.*, 45: 555-564 {1983}; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004).

NAGLU polypeptides contemplated include, but are not limited to, a NAGLU polypeptide with the amino acid sequence set out in SEQ ID NO: 2.

SGSH polypeptides contemplated include, but are not limited to, a SGSH polypeptide with the amino acid sequence set out in SEQ ID NO: 4.

The polypeptides contemplated include full-length proteins, precursors of full length proteins, biologically active subunits or fragments of full length proteins, as well as biologically active analogs (e.g., derivatives and variants) of any of these forms of polypeptides. Thus, polypeptides include, for example, those that (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 25, about 50, about 100, about 200, about 300, about 400, or more amino acids, to a polypeptide encoded by a nucleic acid or an amino acid sequence described herein.

As used herein "biologically active derivative," "biologically active fragment," "biologically active analog" or "biologically active variant" includes any derivative or fragment or analog or variant of a molecule having substantially the same functional and/or biological properties of said molecule, such as enzymatic activities.

An "analog," such as a "variant" or a "derivative," is a compound substantially similar in structure to and having the same biological activity as, albeit in certain instances to a differing degree, a naturally-occurring molecule.

A "derivative," for example, is a type of analog and refers to a polypeptide sharing the same or substantially similar structure as a reference polypeptide that has been modified, e.g., chemically.

A polypeptide variant, for example, is a type of analog and refers to a polypeptide sharing substantially similar structure and having the same biological activity as a reference polypeptide (i.e., "native polypeptide" or "native therapeutic protein"). Variants differ in the composition of their amino acid sequences compared to the naturally-occurring polypeptide from which the variant is derived, based on one or more mutations involving (i) deletion of one or more amino acid residues at one or more termini of the polypeptide and/or one or more internal regions of the naturally-occurring polypeptide sequence (e.g., fragments), (ii) insertion or addition of one or more amino acids at one or more termini (typically an "addition" or "fusion") of the polypeptide and/or one or more internal regions (typically an "insertion") of the naturally-occurring polypeptide sequence or (iii) substitution of one or more amino acids for other amino acids in the naturally-occurring polypeptide sequence.

Variant polypeptides include insertion variants, wherein one or more amino acid residues are added to a therapeutic protein amino acid sequence of the present disclosure. Insertions may be located at either or both termini of the protein, and/or may be positioned within internal regions of the therapeutic protein amino acid sequence. Insertion variants, with additional residues at either or both termini, include for example, fusion proteins and proteins including amino acid tags or other amino acid labels.

In deletion variants, one or more amino acid residues in a therapeutic protein polypeptide as described herein are removed. Deletions can be effected at one or both termini of the therapeutic protein polypeptide, and/or with removal of one or more residues within the therapeutic protein amino acid sequence. Deletion variants, therefore, include fragments of a polypeptide sequence.

In substitution variants, one or more amino acid residues of a therapeutic protein polypeptide are removed and replaced with alternative residues. In one aspect, the substitutions are conservative in nature and conservative substitutions of this type are well known in the art. Alternatively, the present disclosure embraces substitutions that are also non-conservative. Exemplary conservative substitutions are described in Lehninger, [Biochemistry, 2nd Edition; Worth Publishers, Inc., New York (1975), pp. 71-77] and are set out immediately below.

| CONSERVATIVE SUBSTITUTIONS | |
| --- | --- |
| SIDE CHAIN CHARACTERISTIC | AMINO ACID |
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

| CONSERVATIVE SUBSTITUTIONS II | |
| --- | --- |
| ORIGINAL RESIDUE | EXEMPLARY SUBSTITUTION |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

In yet further aspect, the invention provides DNA plasmids comprising rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

In another aspect, the invention provides rAAV (i.e., infectious encapsidated rAAV particles) comprising a rAAV genome of the invention. In some embodiments of the invention, the rAAV genome is a self-complementary genome.

The invention includes, but is not limited to, the exemplified rAAV named "rAAV9-CMV-hNAGLU." The rAAV genome has in sequence an AAV2 ITR, the cytomegalovirus (CMV) immediate early promoter/enhancer, an SV40 intron (SD/SA), the NAGLU DNA set out in SEQ ID NO: 1, a polyadenylation signal sequence from bovine growth hormone and another AAV2 ITR. The DNA sequence of the vector genome is set out in SEQ ID NO: 5. The genome lacks AAV rep and cap DNA, that is, there is no AAV rep or cap DNA between the ITRs of the genome.

The invention also includes, but is not limited to, rAAV encoding SGSH. In some embodiments, the rAAV genome has in sequence an AAV2 ITR, the CMV immediate early promoter/enhancer, the SGSH DNA set out in SEQ ID NO: 3, a polyadenylation signal sequence from bovine growth hormone and a AAV2 ITR lacking the terminal resolution site. In some embodiments, the rAAV genome has in sequence an AAV2 ITR, the mouse U1a promoter, the SGSH DNA set out in SEQ ID NO: 3, a polyadenylation signal sequence from bovine growth hormone and a AAV2 ITR lacking the terminal resolution site. In some embodiments, rAAV genome has in sequence an AAV2 ITR, the mouse U1a promoter, an intron, the SGSH DNA set out in SEQ ID NO: 3, a polyadenylation signal sequence from bovine growth hormone and a AAV2 ITR lacking the terminal resolution site. The genomes lack AAV rep and cap DNA, that is, there is no AAV rep or cap DNA between the ITRs of the genomes.

NAGLU and SGSH DNAs include, without limitation, those that (1) hybridize under stringent hybridization conditions to a nucleic acid encoding an amino acid sequence as described herein, and conservatively modified variants thereof; (2) have a nucleic acid sequence that has greater than about 95%, about 96%, about 97%, about 98%, about 99%, or higher nucleotide sequence identity, over a region of at least about 25, about 50, about 100, about 150, about 200, about 250, about 500, about 1000, or more nucleotides (up to the full length sequence of the mature protein), to a nucleic acid sequence as described herein. Exemplary "stringent hybridization" conditions include hybridization at 42° C. in 50% formamide, 5×SSC, 20 mM Na.PO4, pH 6.8; and washing in 1×SSC at 55° C. for 30 minutes. It is understood that variation in these exemplary conditions can be made based on the length and GC nucleotide content of the sequences to be hybridized. Formulas standard in the art are appropriate for determining appropriate hybridization conditions. See Sambrook et al., Molecular Cloning: A Laboratory Manual (Second ed., Cold Spring Harbor Laboratory Press, 1989) §§ 9.47-9.51.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69: 427-443 (2002); U.S. Pat. No. 6,566,118 and WO 98/09657.

In an additional aspect, the invention contemplates compositions comprising rAAV of the present invention encoding an NAGLU polypeptide. These compositions may be used to treat mucopolysaccharidosis IIIB. In other embodiments, compositions of the present invention may include two or more rAAV encoding different polypeptides of interest.

In still an additional aspect, the invention contemplates compositions comprising rAAV of the present invention encoding an SGSH polypeptide. These compositions may be used to treat mucopolysaccharidosis IIIA. In other embodiments, compositions of the present invention may include two or more rAAV encoding different polypeptides of interest.

Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). Dosages may also vary based on the timing of the administration to a human. These dosages of rAAV may range from about $1\times10^{11}$ vg/kg, about $1\times10^{12}$, about $1\times10^{13}$, about $1\times10^{14}$, about $1\times10^{15}$, about $1\times10^{16}$ or more viral genomes per kilogram body weight in an adult. For a neonate, the dosages of rAAV may range from about $1\times10^{11}$, about $1\times10^{12}$, about $3\times10^{12}$, about $1\times10^{13}$, about $3\times10^{13}$, about $1\times10^{14}$, about $3\times10^{14}$, about $1\times10^{15}$, about $3\times10^{15}$, about $1\times10^{16}$, about $3\times10^{16}$ or more viral genomes per kilogram body weight.

Treatment by methods of the invention comprises the step of administering an intravenous (IV) effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival.

Combination therapies are also contemplated by the invention. Combination as used herein includes both simultaneous treatment or sequential treatments. Combinations of methods of the invention with standard medical treatments (e.g., transient or long-term immunosuppression) are specifically contemplated, as are combinations with novel therapies.

Compositions suitable for systemic (IV) use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin, and Tween family of products (e.g., Tween 20).

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction of cells with rAAV of the invention results in sustained expression of NAGLU or SGSH polypeptide. Transduction may be carried out with gene cassettes comprising tissue specific control elements, for example, promoters that allow expression specifically within neurons or specifically within astrocytes. Examples include neuron specific enolase and glial fibrillary acidic protein promoters. Inducible promoters under the control of an ingested drug may also be developed.

It will be understood by one of ordinary skill in the art that a polynucleotide delivered using the materials and methods of the invention can be placed under regulatory control using systems known in the art. By way of non-limiting example, it is understood that systems such as the tetracycline (TET on/off) system [see, for example, Urlinger et al., *Proc. Natl. Acad. Sci. USA* 97(14):7963-7968 (2000) for recent improvements to the TET system] and Ecdysone receptor regulatable system [Palli et al., *Eur J. Biochem* 270: 1308-1315 (2003] may be utilized to provide inducible polynucleotide expression.

Thus, the invention provides methods of systemically administering an effective dose (or doses, administered essentially simultaneously or doses given at intervals) of rAAV of the invention to a patient in need thereof.

BRIEF DESCRIPTION OF THE DRAWING

FIG. 2a. Hidden task in water maze (n=11/group). Day 1: test trial. FIG. 2b. Latency to fall from a rotarod (n=11/group). FIG. 2c. Survival (i 5/group, P<0.001). +/+: wt; −/−: MPS IIIB; AAV9-L, AAV9-H: MPS IIIB mice treated with $5 \times 10^{12}$ or $1.5 \times 10^{13}$ vg/kg rAAV9-hNAGLU vector, respectively. *: P<0.05 (vs. +/+); #: P<0.05 (vs. AAV9-L); ^: P<0.05 (vs. AAV9-H); &: P>0.05 (vs. −/−). Repeated measures ANOVA analyses: @: day effect P<0.01; $: group (treatment effect) P<0.01; %: day-group interaction P41.020 (rotarod).

FIG. 3a. Dose-response. +/+: wt; AAV9-11, AAV9-L: MPS IIIB mice treated with $1.5 \times 10^{13}$(AAV9-H) or $5 \times 10^{12}$ vg/kg (AAV9-L) vector; FIG. 3b. Impact of mannitol pretreatment. M+/M−: MPS IIIB mice treated with $2 \times 10^{13}$ vg/kg vector with (M+) or without (M−) mannitol pretreatment. FIG. 3c. Plasma NAGLU activity (n=3-4). +/−: heterozygotes. No significant difference in tissue NAGLU activity was detected at 6 and 9 months pi. Data shown are means±SD of combined data on tissues from mice at 6 and 9 mo pi. *: P<0.01 vs. +/+; #: P<0.05 vs. AAV9-H or M+: P>0.05 vs. +/+. @: P<0.05 vs. +/−.

FIG. 4a. Dose response. FIG. 4b. Impact of mannitol pretreatment. +/Ai wt; −/−: MPS IIIB; AAV9-H, AAV9-L: MPS MB mice treated with 1.5× 1013 vg or 5×1012 vg/kg vector; M+, M−: MPS IIIB mice treated with rAAV9 vector (2×1013 vg/kg) with or without mannitol pretreatment. Data shown are means±SD (n=5-6), combining data from tissues collected at 6 and 9 mo pi. *: P<0.01 vs. +/+; #: P<0.05 vs. AAV9-H or M+; ^: P<0.05 vs. AAV9-L or M−; +: P>0.05 vs. +/+.

FIG. 5a. Number of astrocytes: Data are means±SD of GFAP+ cells per 330×433 pm on 6-8 IF-GFAP-staining sections/mouse, from 3 mice/group. FIG. 5b. Number of purkinje cells: Data are means±SD of purkinje cells/200 p.m (in length) in ansiform lobules in cerebellum on 6 toluidine blue stained sections/mouse, from 3 mice/group. NT: non-treated MPS IIIB mouse; AAV9: MPS IIIB mouse treated with rAAV9. CTX: cerebral cortex; ST: Striatum; TH: thalamus; BS: Brain stem. *: P<0.01 vs. non-treated.

DETAILED DESCRIPTION

The present invention is illustrated by the following examples relating to delivery of human NAGLU (hNAGLU) genes to the spinal cord via intravenous delivery of rAAV9. Example 1 describes rAAV encoding hNAGLU. Example 2 describes the administration of the rAAV encoding hNAGLU to MPSIIIB mice. Examples 3 through 6 describe the beneficial results of administration of the rAAV. Example 7 discusses the significance of the results. Example 8 describes rAAV encoding SGSH. Examples 9 through 11 describe administration of various dosages of rAAV encoding SGSH to MPSIIIA mice of varying ages, as well as the beneficial effects of the administration.

Example 1

Recombinant AAV (rAAV) Viral Vectors Encoding NAGLU

A rAAV vector plasmid, containing AAV2 ITRs, an immediate early CMV promoter/enhancer, an SV40 intron, a human α-N-acetylglucosaminidase coding region, a bGH polyadenylation signal sequence, and ampicillin resistance gene, was used to produce a rAAV9-CMV-hNAGLU viral vector.

Figure 1:
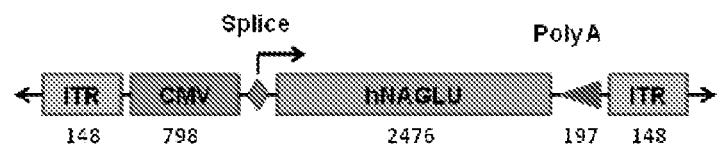
FIG. 1 is a map of the rAAV-CMV-hNAGLU vector genome.

Recombinant AAV9 viral vectors with the hNAGLU-encoding genome were produced in 293 cells using three-plasmid co-transfection, and purified as described in Zolotukhin et al., Gene Ther., 6: 973-985 (1999). This vector is referred to as "rAAV9-CMV-hNAGLU" herein. The vector genomes contained minimal elements required for transgene expression, including AAV2 terminal repeats, a human cytomegalovirus (CMV) immediate-early promoter, SV40 splice donor/acceptor signal, a human NAGLU coding sequence (SEQ ID NO: 1), and bGH polyadenylation signal. SEQ ID NO: 5 is the DNA sequence of the vector genome. FIG. 1 is a map of the vector genome wherein the length of the various elements of the genome is indicated below the element.

A control self-complementary AAV encoding green fluorescent protein, scAAV9-CMV-GFP was also produced, containing AAV2 terminal repeats, a human cytomegalovirus (CMV) immediate-early promoter, SV40 splice donor/acceptor signal, a eGFP coding sequence, and SV40 polyadenylation signal.

Example 2

Administration of Viral Vectors

An MPS IIB3 knock-out mouse colony [Li et al., Proc. Natl. Acad. Sci. USA, 96: 14505-14510 (1999) was maintained on an inbred background (C57BL/6) of backcrosses of heterozygotes. All care and procedures were in accordance with the *Guide for the Care and Use of Laboratory Animals* [DHHS Publication No. (NIH) 85-23]. The genotypes of progeny mice were identified by PCR.

To assess the therapeutic efficacy of rAAV9 gene delivery, 4-6-week-old MPS IIIB mice were treated with an IV injection of rAAV9-CMV-hNAGLU ($5 \times 10^{12}$ or $1.5 \times 10^{13}$ vg/kg, n=11/group). Separately, other MPS IIIB mice were treated with $2 \times 10^{13}$ vg/kg rAAV9-CMV-hNAGLU, with or without mannitol pretreatment (n=5/group), to assess the impact on CNS entry. Controls were sham-treated (phosphate-buffered saline) wild type (wt) and MPS IIIB littermates (n=11). Tissue analyses were carried out at 6 months and 9 months (n=2-4/group) post-injection (pi).

Additionally, self-complementary AAV (scAAV) vector carrying a cytomegalovirus-green fluorescent protein (CMV-GFP) transgene ($5 \times 10^{12}$ vg/kg) was injected IV into 6-8-week-old wt mice (n=4/group) to determine the distribution of transgene expression (1 month pi), as a comparison to rAAV9-hNaGlu treatment.

Results are presented below.

Example 3

Behavioral Tests

The rAAV9-CMV-hNaGlu-treated MPS BIB mice and controls were tested for behavioral performance at approximately 5.0-5.5 months of age as follows.

Hidden Task in the Morris Water Maze

Figure 2:
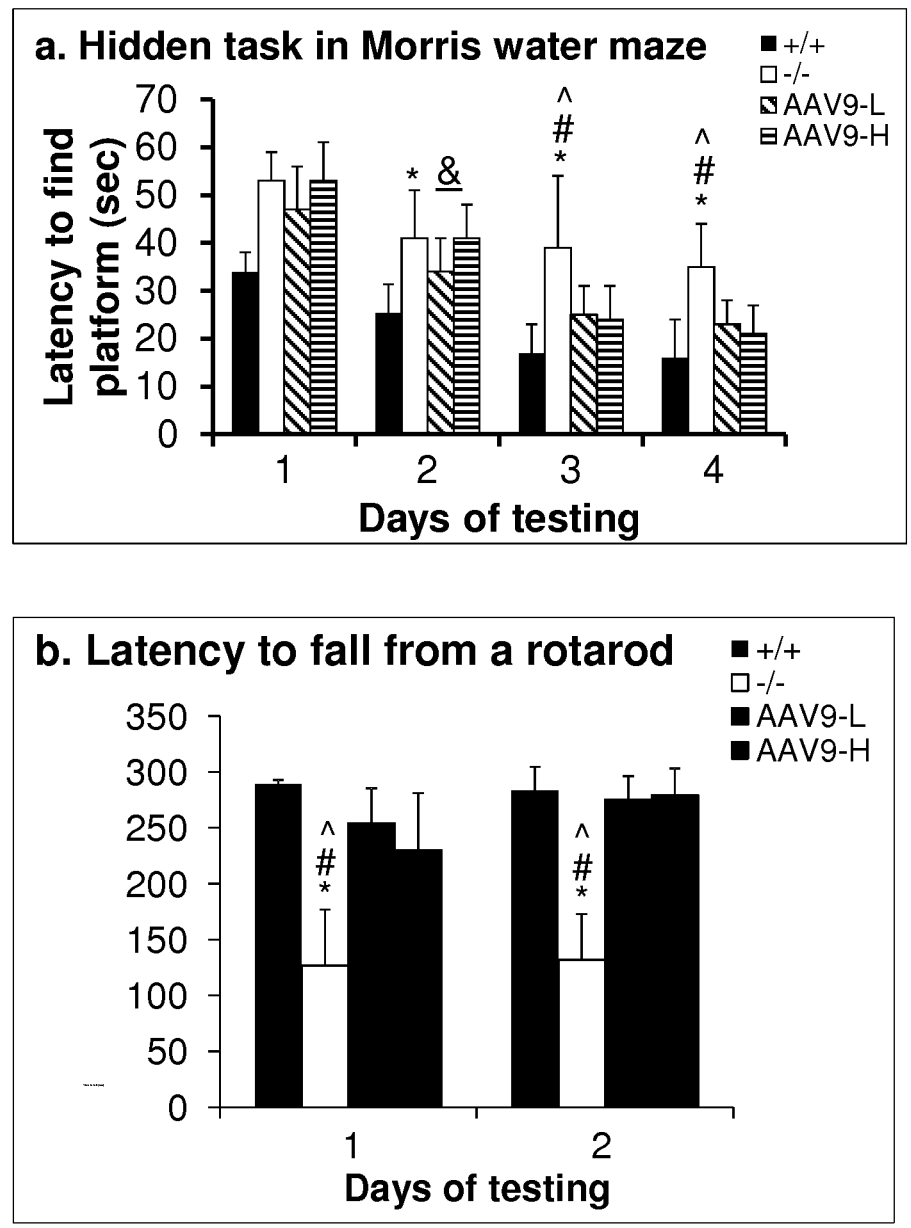
FIG. 2 shows improved behavior and extended survival in MPS IIIB mice after systemic gene transfer by rAAV-CMV-hNAGLU.
Figure 2:
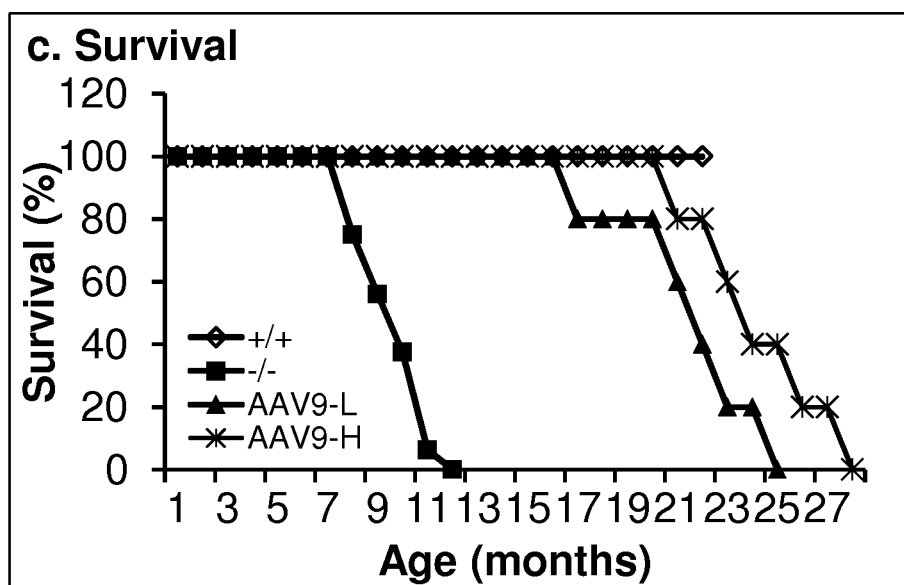

A water maze (diameter=122 cm) was filled with water (45 cm deep, 24-26° C.) containing 1% white TEMPERA paint, located in a room with numerous visual cues. See Warburton et al., *J. Neurosci*, 21: 7323-7330 (2001). Mice were tested for their ability to find a hidden escape platform (20×20 cm) 0.5 cm under the water surface. Each animal was given four trials per day, across three days, as described previously. Measures were taken of latency to fmd the platform (sec) via an automated tracking system (San Diego Instruments). Results are shown in FIG. 2a.

Rotarod

Mice were tested on an accelerating rotarod (Med Associate, Inc.) to assess motor coordination. See Lijam et al., *Cell*, 90895-905 (1997). Rotation speed was set at an initial value of 3 revolutions per minute (rpm), with a progressive increase to a maximum of 30 rpm across five minutes (the maximum trial length). For the first test session, animals were given three trials, with 45 seconds between each trial. Two additional trials were given 48 hours later. Measures were taken for latency to fall from the top of the rotating barrel. Results are shown in FIG. 2b.

Statistical Analyses

Means, standard deviation (SD) and unpaired student t-test were used to analyze quantitative data. Behavioral measures were taken by an observer blind to experimental treatment. Behavioral testing data were also analyzed using repeated measures ANOVA (SAS 9.1.3) to determine the significance of the variances among treatment and control groups and testing days.

Results of Behavioral Tests

All mice treated IV with $5 \times 10^{12}$ or $1.5 \times 10^{13}$ vg/kg rAAV9-NAGLU were tested for behavior at 5-5.5 mo of age to assess the neurological impacts. Both dosage groups exhibited significant decreases in latency to find a hidden platform in a water maze (FIG. 2a), and significantly longer latency to fall from an accelerating rotarod (FIG. 2b), compared with non-treated MPS IIIB mice, indicating the correction of cognitive and motor function. There were no significant differences in behavior performance between these two dose groups.

Example 4

Longevity Assessment

Following the rAAV9-hNaGlu vector injection(s), mice were continuously observed for the development of endpoint symptoms, or until death occurred. The endpoint was when the symptoms of late stage clinical manifestation (urine retention, rectal prolapse, protruding penis) in MPS IIIB mice became irreversible, or when wt control mice were 24 months or older. Longevity data were analyzed using Kaplan-Meier method. The significance level was set at $P<0.05$. Results are shown in FIG. 2c.

Ten rAAV9-treated MPS IIIB mice, five from each dose group, were observed for longevity. All ten survived >16.9 months (with one mouse of the low-dose group dying at age of 16.1 months) and the majority of them survived 18.9-27.4 months within the normal range of lifespan, while all non-treated MPS IIIB mice died at 8-12 months of age (P<0.001) (FIG. 2c). These data demonstrate that a single IV rAAV9 vector injection alone is functionally beneficial in treating the CNS disease and increasing longevity in MPS IIIB mice.

Example 5

Tissue Analyses

In the therapeutic studies above, tissue analyses were carried out at 6 mo and 9 mo post injection (pi). Mice were anesthetized with 2.5% Avertin before tissue collection. Brain, spinal cord and multiple somatic tissues were collected on dry ice or embedded in OCT compound and stored at −70° C., before being processed for analyses. Tissues were also processed for paraffin sectioning.

Tissue samples from scAAV9-GFP vector-treated mice were collected for analysis 4-5 weeks pi. The mice were anesthetized with 2.5% Avertin and then perfused transcardially with cold PBS (0.1M, pH7.4), followed by 4% paraformaldehyde in phosphate buffer (0.1M, pH7.4). The entire brain and spinal cord, as well as multiple somatic tissues (including liver, kidney, spleen, heart, lung, intestine and skeletal muscles), were collected and fixed in 4% paraformaldehyde overnight at 4° C. before being further processed for vibratome sectioning.

NAGLU Activity Assay

Figure 3:
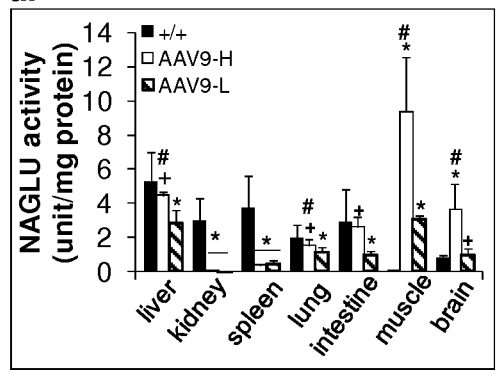
FIG. 3 shows rAAV9-mediated expression of functional rNAGLU in tissues. Tissues from MPS IIIB mice treated with rAAV9-hNAGLU were assayed for NAGLU activity (6 and 9 mo pi)(n=5-6/group).
Figure 3:
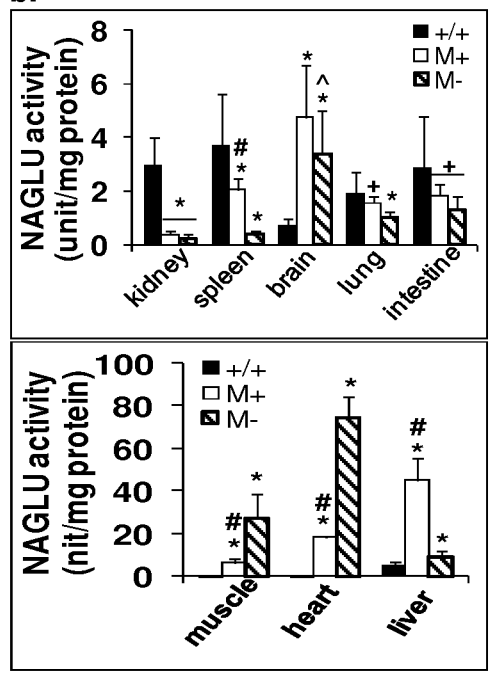
Figure 3:
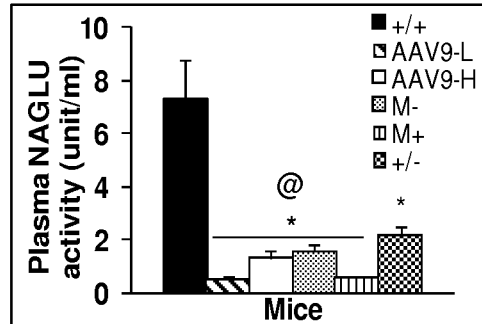

Tissues were analyzed at 6 mo and/or 9 mo pi by NAGLU activity assay to determine the distribution and level of rAAV9-mediated transgene expression. Tissue samples were assayed for NaGlu enzyme activity following a published procedure with modification. The assay measures 4-methylumbelliferone (4MU), a fluorescent product formed by hydrolysis of the substrate 4-methylumbellireyl-N-acetyla-D-glucosaminide. The NaGlu activity is expressed as unit/mg protein. 1 unit is equal to 1 nmol 4MU released/h at 37° C. Results are shown in FIG. 3.

GAG Content Measurement

Figure 4:
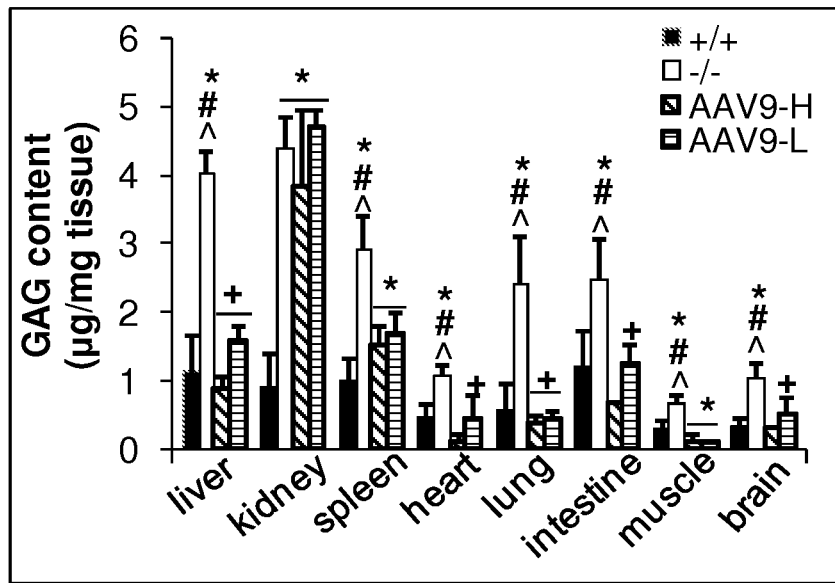
FIG. 4 shows the significant reduction of GAG content in the CNS and somatic tissues. Tissues from MPS IIIB mice treated with rAAV9-hNAGLU were assayed to quantify GAG content (6 and 9 mo pi).
Figure 4:
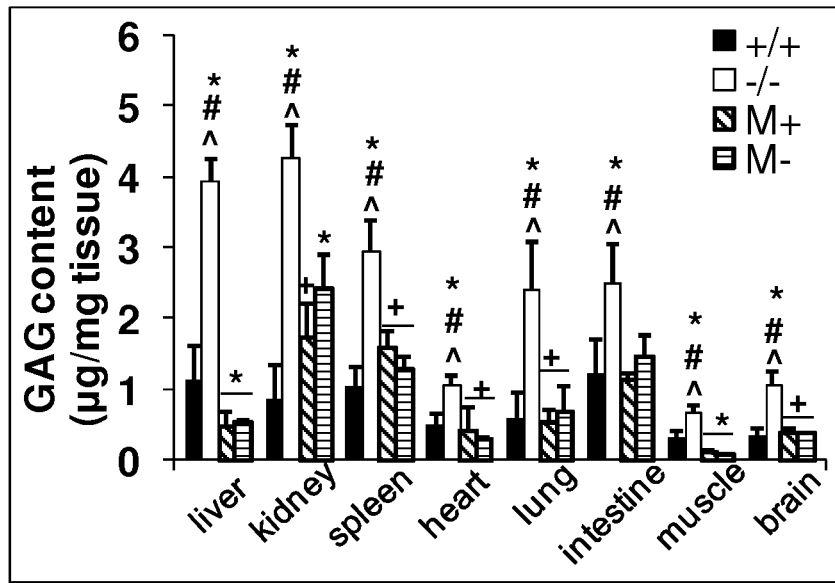

GAG was extracted from tissues following published procedures [van de Lest et al., *Anal. Biochem.* 221: 356-361(1994)] with modification [Fu et al., *Gene Ther.*, 14: 1065-1077 (2007). Dimethylmethylene blue (DMB) assay was used to measure GAG content [de Jong et al., *Clin. Chem.*, 35: 1472-1477 (1989)]. The GAG samples (from 0.5-1.0 mg tissue) were mixed with $H_2O$ to 40 ml before adding 35 nM DMB (Polysciences CEO 03610-1) in 0.2 mM sodium formate buffer (SFB, pH 3.5). The product was measured using a spectrophotometer (0D535). The GAG content was expressed as μg/mg tissue. Urine GAG content was also measured. Heparan sulfate (Sigma, H9637) was used as standard. Results are shown in FIG. 4.

Immunofluorescence

Immunofluorescence (IF) was performed to identify cells expressing hNAGLU, GFP or glial fibrillary acidic protein (GFAP) for astrocytes, using antibodies against hNaGlu (a kind gift from Dr. E F Neufeld, UCLA), GFP (Invitrogen) or GFAP (Chemicon), and corresponding secondary antibody conjugated with AlexaFluor[568] or AlexaFluor[488] (Molecular Probes). The IF staining was performed on thin cryostat sections (8 p.m) of tissue samples following procedures recommended by the manufacturers. The sections were visualized under a fluorescence microscope.

Histopathology

Tissues were assayed for histopathology to visualize the impact of IV rAAV9-NAGLU gene delivery on the lysosomal storage pathology in MPS IIIB mice. Histopathology was performed following standard methods. Paraffin sections (41.un) were fixed with 4% paraformaldehyde in phosphate buffer (0.1 M, pH 7.2) at 4° C. for 15 min and stained with 1% toluidine blue at 37° C. for 30 min to visualize lysosomal GAG. The sections were mounted, and imaged under a light microscope.

Quantitative Real Time PCR

Total DNA was isolated from tissue samples of treated and nontreated MPS IIIB mice using Qiagen DNeasy columns. Brain DNA was isolated from midbrain tissue. The DNA samples were analyzed by quatitative real-time PCR, using Absolute Blue QPCR Mix (Thermo Scientific, Waltham, Mass.) and Applied Biosystems 7000 Real-Time PCR System, following the procedures recommended by the manufacturer. Taqman primers specific for the CMV promoter were used to detect rAAV vector genomes: f: GGCAGTACATC AAGTGTATC (SEQ ID NO: 6); r: ACCAATGG TAATAG CGATGAC (SEQ ID NO: 7); probe: [6~FAM]AATGACGGTAAAT GGCCCGC [TAMRA~6~FAM] (SEQ ID NO: 8). Genomic DNA was quantified in parallel samples using β-actin specific primers: f: GTCATCAC TATTG GCAACGA (SEQ ID NO: 9); r: CTCAGGAGTTTTGTCACCTT (SEQ ID NO: 10); probe: [6~FAM]TTCCGATGCCCT GAGGCTCT[Tamra~Q] (SEQ ID NO: 11). Genomic DNA from nontreated MPS IIIB mouse tissues was used as controls for background and absence of contamination. Global CNS and widespread somatic restoration of NAGLU.

Tissue Analysis Results

Tissues were analyzed at 6 months and/or 9 months pi by immunofluorescence (IF) and NAGLU activity assay to determine the distribution and level of rAAV9-mediated transgene expression. NAGLU-specific IF was detected throughout the brains of treated mice, in neurons, glia, and abundant endothelial cells in capillaries and larger blood vessels, in an apparently dose-dependent fashion. No significant differences were observed in the distribution or levels of rNaGlu signal between 6 months and 9 months pi. NAGLU-positive glial cells were not costained with anti-glial fibrillary acidic protein (GFAP) Ab, and were likely to be oligodendrocytes, based on their morphology. Importantly, while rNAGLU IF was observed in the brains of all rAAV9-treated mice, mannitol pretreatment did appear to increase the number of transduced cells in the CNS.

Differential transduction levels were observed in peripheral organs. The rNAGLU protein was detected in 20-40% of hepatocytes, >95% of cardiomyocytes, and 10-30% of skeletal myocytes. The distribution of rAAV9-transduced hepatocytes was uniform throughout the liver. Transduction in abundant neurons in myenteric plexus and submucosal plexus of the intestine was observed, suggesting efficient targeting of the peripheral nervous system (PNS). The rNAGLU signals were mostly present in granules, whereas scAAV9-mediated GFP signals were uniform in the cytoplasm of transduced cells, suggesting correct lysosomal trafficking of rNAGLU. Transduction of endothelial cells was also observed in peripheral tissues of rAAV9-GFP vector-treated mice.

Example 6

Enzyme Function Assays

Function of the recombinant NAGLU and resulting effects in animals were also analyzed in the therapeutic studies above.

rNAGLU Enzymatic Function

Transgene enzymatic activity was assayed to quantify the expression and the functionality of rAAV9-mediated rNAGLU. There were no significant differences in tissue NAGLU activity at 6 and 9 months pi, suggesting stable transduction. The rAAVmediated rNaGlu was metabolically functional and the tissue rNAGLU activity was dose-dependent, with approximately normal levels in the brains of mice receiving $5 \times 10^{12}$ vg/kg vector, and supra-physiologic levels in the brains of mice receiving $1.5 \times 10^{13}$ vg/kg (FIG. 3a). In both dose groups, we detected NAGLU activity at normal or subnormal levels in the liver, lung and intestine (FIG. 3a), supra-physiologic levels in the skeletal muscles (FIG. 3a) and heart (40 & 100 units/mg protein, data not shown), and low levels in the spleen, but no detectable NAGLU activity in the kidney. A low level of NAGLU activity was detected in the kidneys of the mice treated with $2 \times 10^{13}$ vg/kg vector (FIG. 3b). Mannitol pretreatment led to an increase in NAGLU activity in the brain (though not significant due to high individual variation), liver, spleen, lung and intestine, but a decrease in the heart and skeletal muscle (FIG. 3b). No detectable NAGLU activity (<0.03 unit/mg) was observed in tissues from non-treated MPS IIIB mice.

rNaGlu Secretion

Plasma samples were assayed for NAGLU activity to assess the secretion of the enzyme. Activity was detected in the plasma of all rAAV9-treated MPS MB mice at or near heterozygote levels, though lower than homozygous wt levels (FIG. 3c). Mannitol pretreatment resulted in significant reduction in plasma NAGLU activity (FIG. 3c). These data indicate that the rNAGLU was secreted, though the source tissue or cell type is not clear.

GAG Content Reduction

Tissues were assayed for GAG content to quantify the impact of IV rAAV9-NAGLU gene delivery on the lysosomal storage pathology in MPS IIIB mice. The single IV rAAV9-NAGLU injection led to a reduction of GAG content to normal levels in the brain, liver, heart, lung, intestine and skeletal muscle in mice of all four treatment groups (FIG. 4). Doses of $5 \times 10^{12}$ µg or $1.5 \times 10^{13}$ vg/kg resulted in partial GAG reduction in the spleen but had no impact in kidney (FIG. 4a).

Treatment with $2 \times 10^{13}$ vg/kg led to a decrease of GAG to normal levels in the spleen, and partial GAG reduction in the kidney (FIG. 4b), consistent with the observed enzyme activity levels.

Histopathology Correction

Histopathology showed complete clearance or reduction of lysosomal storage lesions in the vast majority of CNS areas, including cerebral cortex, thalamus, brain stem, hippocampus, and spinal cord in all four treatment groups. There were decreases in the size, number of vacuoles, and number of cells with lysosomal storage lesions, even in the few brain areas that did not show a complete correction, such as purkinje cells and cells in the striatum and hypothalamus. Importantly, the majority of brain and spinal cord parenchymal cells exhibited a well defined normalized morphology. Immunofluorecence detection for the lysosomal marker, LAMP-1, showed that IV infusion of rAAV9-NAGLU vector at all doses also resulted in marked reduction of LAMP-1 signal, especially in neurons, throughout the brain. This further supports the conclusion that the amount of vector crossing the BBB was sufficient for efficient correction of CNS lysosomal storage pathology.

In somatic tissues, complete clearance of lysosomal storage lesions in the livers of all rAAV9-hNaGlu treated mice was observed as well as attenuation of nuclear shrinkage, a marker of cell stress and damage.

Correction of Gliosis and Neurodegeneration

Figure 5:
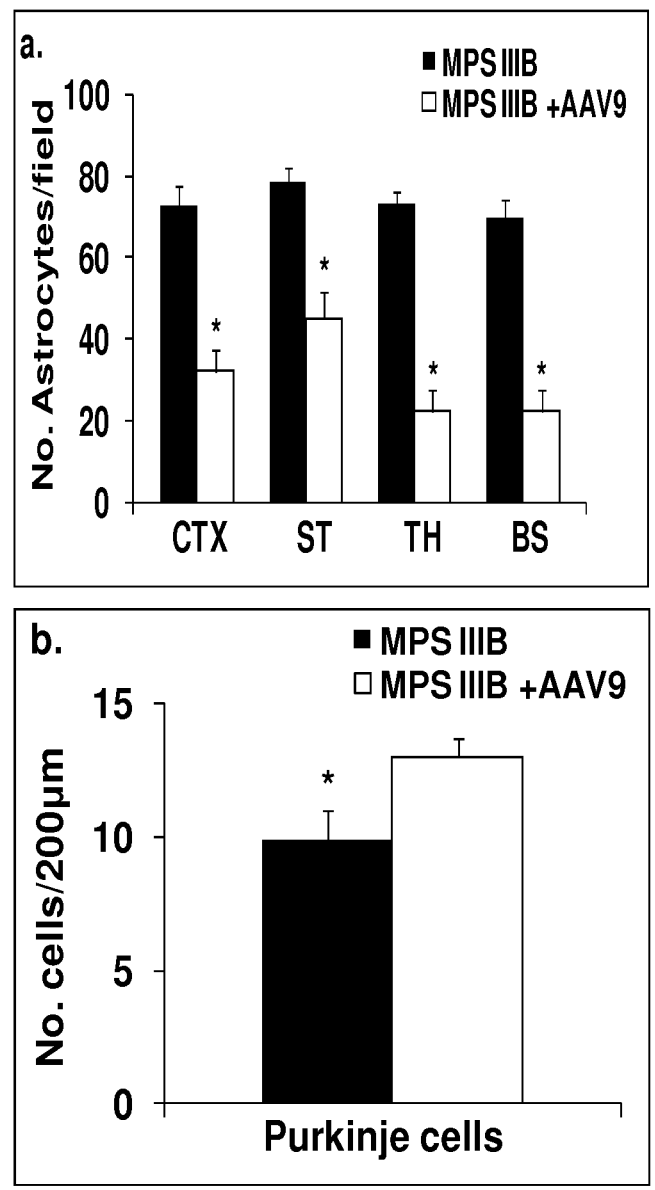
FIG. 5 shows rAAV9-mediated correction of astrocytosis and neurodegeneration in MPS IIIB mice. Brain sections of MPS IIIB mice treated with rAAV9-CMV-hNAGLU vector (6 mo pi) were assayed for GFAP by immunofluorescence and stained with toluidine blue for histopathology.

In order to determine whether the rAAV9-hNaGlu vector delivery had an impact on astrocytosis, a major secondary neuropathology of MPS IIIB, brain sections were assayed by immunofluorecence for GFAP expressing cells. Significant decreases in astrocyte numbers in gray matter throughout the brain of treated mice were observed compared to untreated at 6 mo and 9 mo pi (FIG. 5a). Histopathology also revealed significant increases in the numbers of neurons, such as Purkinje cells (FIG. 5b), in the brains of treated MPS IIIB mice. These data strongly indicate the amelioration of astrocytosis and neurodegeneration, which are hallmarks of secondary neuropathologies in MPS IIIB, in response to the rAAV9 treatment.

Vector Genome Distribution

Quantitative real-time PCR was performed to compare the amount of rAAV9-CMV-hNaglu vector entering the CNS versus somatic tissues. Table 1 shows the distribution of the vector genome in different tissues/organs of MPS IIIB mice treated with IV vector injection at varying doses. The highest concentrations of vector genome were detected in liver (8.20±4.73-32.09±3.93 copies/cell), followed by heart (0.07-0.22 copies/cell), and brain (0.06±0.001-0.15±0.02 copies/cell), and very low copy numbers were detected in other tissues/organs (Table 1). This differential vector distribution in rAAV9-treated MPS IIIB mice largely correlated with the distribution of rNAGLU IF and enzymatic activity. Notably, mannitol pretreatment increased the vector copy numbers in the brain, correlating with brain NAGLU activity levels. Furthermore, these data reflect persistence of vector genome distribution in treated mice at 6 months pi, supporting a stable long-term transduction. Levels of vector genome copies correlating with rNAGLU activity and distribution were not detectable, possibly due to difficulties in quantitative isolation of DNA from muscle tissue.

TABLE 1

Estimated vector genome in the liver and brain of rAAV9-treated mice

| Mice | n | Vector genome (copy/cell) | | |
|---|---|---|---|---|
| | | Liver | Brain | Heart |
| rAAV9-L | 2 | 8.20 ± 4.73 | 0.07 ± 0.07 | 0.07* |
| rAAV9-H | 3 | 10.86 ± 2.94 | 0.09-10.47 | 0.13 ± 0.07 |
| rAAV9-M− | 2 | 21.97 ± 6.43 | 0.06 ± 0.001 | 0.22* |
| rAAV9-M+ | 3 | 32.09 ± 3.93 | 0.15 ± 0.02 | 0.14* |
| Non-treated | 1 | 0.000 | 0.000 | 0.00 |

Mouse tissue samples (6 mo pi) were assayed in duplicates for vector genome copy numbers by qPCR.
Data is expressed as vector copy/cell (means ± SD).
rAAV9-L: IV infusion of $5 \times 10^{12}$ vg/kg;
rAAV9-H: IV infusion of $1.5 \times 10^{13}$ vg/kg;
rAAV9-M−: IV infusion of $2 \times 10^{13}$ vg/kg without mannitol pretreatment;
rAAV9-M+: IV infusion of $2 \times 10^{13}$ vg/kg following mannitol pretreatment.
*Data from 1 sample in duplicates.

Example 7

Discussion

This study demonstrates the first significant therapeutic benefit for treating MPS IIIB in adult animals from systemic gene delivery to the CNS without additional treatment to disrupt the BBB. A single IV injection of hNAGLU-expressing rAAV9 vector was sufficient to significantly improve cognitive and motor functions, and greatly prolong survival in MPS IIIB mice. In the present study using rAAV9, the increased longevity exceeds the outcome of previous studies using rAAV2 vector delivered through either intracisternal injection, or systemic injection following mannitol pretreatment. The rNAGLU enzyme was clearly secreted and functional, leading to a significant bystander effect, and efficient degradation of heparan sulfate GAG in CNS tissues. Importantly, the clinically meaningful therapeutic benefits of the IV-delivered rAAV9 vector in MPS IIIB mice were achieved at a lower dose than the mannitol-facilitated, systemically delivered rAAV2 vector. The enhanced rAAV9-CNS transduction in response to mannitol pretreatment suggests further potential for reducing the vector dose, and the attendant risk and burden to patients.

The IV vector injection resulted in a ubiquitously diffuse, global rAAV9-NaGlu transduction throughout the CNS, reflecting the expected distribution pattern for vascular delivery. This contrasts sharply with the focal gradient distribution typically achieved through direct brain parenchymal injection, or the periventricular transduction pattern from intracisternal and intraventricular injection. While similar to the pattern of transgene expression from IV-delivered rAAV2 after mannitol pretreatment, the extent of rAAV9 transduction was significantly higher in all areas of the brain. This correlates with the increased effects on longevity and cognitive function compared to that previously achieved using rAAV2-mannitol treatment, and the normal or above normal levels of NAGLU activity in the CNS. These findings strongly support the use of the trans-BBB neurotropic rAAV9 as a vector for CNS gene therapy and reinforce the view that efficient CNS delivery is the most critical issue for developing therapies to treat MPS IIIB.

The rAAV9-transduced CNS cells include neurons, glia and endothelia. Neuronal cell transduction appears to be non-preferential, including most types of neurons throughout the brain. In contrast, the transduction of glial cells appears to be cell-type specific, targeting predominantly oligodendrocyte-like cells, though it is unclear whether this is a receptor- or promoter-specific phenomenon. In a previous report [Faust et al., supra] describing predominant transduction of astocytes after systemic injection of rAAV9 vector in adult mice, a hybrid chicken J3-actin/CMV-enhancer promoter was used, rather than the CMV enhancer-promoter used in the present study.

In normal cells, 5-20% of newly synthesized lysosomal protein is secreted and available to be taken up by neighboring cells, leading to the by-stander effect. The widespread clearance/reduction of lysosomal storage pathology, and normalized tissue GAG content, strongly support an efficient by-stander effect from the rAAV9-'mediated rNAGLU. The abundant transduction of endothelial cells in the brain may be an important contributor to the effectiveness of rAAV9 gene delivery for MPS IIIB because of the close association between CNS cells and brain microvascular endothelial cells, which together constitute the neurovascular unit. While the observed high levels of rNAGLU expression stem from the transduction of a relatively small number of CNS cells, it is sufficient to correct the neuropathology leading to functional correction of the neurological disorders.

The rAAV9 treatment also led to a regular morphology in CNS cells, and the correction of major secondary neuropathology, astrocytosis, and neurodegeneration. It is worth noting that this level of correction of CNS pathology was not achieved in previous studies using rAAV2-hNAGLU vector with mannitol. While neuropathology is the primary cause of mortality in MPS IIIB patients, somatic correction may provide additional therapeutic benefits, since lysosomal storage pathology inevitably manifests in virtually all organs. The IV-delivered rAAV9 exhibited broad tropism in peripheral tissues in a distinct pattern, as previously reported, reflecting extensive extravasation and cell-type specific transduction. This led to complete, longterm correction of lysosomal storage in multiple somatic tissues even at a relatively low dose. Again, relatively low levels of transduction in some tissues were associated with clearance of lysosomal storage of GAGs in the organs, consistent with a significant contribution from the by-stander effect of secreted rNAGLU enzyme. It is not clear whether the by-stander correction in peripheral tissues is mediated by enzyme secreted from neighboring cells within the same tissue, or circulating rNAGLU secreted by more extensively transduced tissues, in a manner analogous to enzyme replacement therapy. However, the observation of partial GAG reduction in the kidney only at the highest vector dose, correlating with detectable transduction in the kidney only at that dose, suggests that the by-stander effect may be primarily local in this tissue. The primary source of circulating NAGLU may be liver, muscle, or endothelium. However, the decrease in plasma levels in response to mannitol pretreatment correlated with decreased transduction in muscle rather than liver, suggesting that liver may not be the primary source.

Another important observation is the efficient transduction of neurons in myenteric plexus and submucosal plexus of the intestine, potentially enabling correction of not only the CNS but also the PNS at all levels via systemic delivery. This suggests that neurotropism is a general property of the AAV9 serotype, and not dependent on the specific structure of the brain neurovascular unit. Broad neurotropism is a valuable property in gene therapy for the treatment of MPS IIIB, considering that lysosomal storage pathology manifests not only in the CNS but also in the PNS.

Example 8

Recombinant AAV (rAAV) Viral Vectors Encoding SGSH

A rAAV vector plasmid was used to produce three different rAAV9-CMV-hSGSH viral vectors.

The three self-complementary AAV hSGSH vector-producing plasmids were constructed using conventional plasmid cloning techniques. Each vector genome contains an SGSH coding region (SEQ ID NO: 3) and either the mouse U1a promoter, with or without an intron, or a CMV promoter without an intron, Each vector genome also contains a bGH polyadenylation signal. Each self-complementary vector plasmid construct contains one intact AA2 terminal repeat and one modified AAV2 terminal repeat missing the terminal resolution site, thereby forcing the replication of dimeric self-complementary DNA genomes. Self-complementary AAV hSGSH viral vectors were produced and packaged in AAV serotype 9 capsids. The viral vectors were tested for expression of hSGSH protein and reduction of GAG storage in human MPS IIIA fibroblasts.

Self-complementary AAV hSGSH viral vectors were tested in an MPS IIIA mouse model having a missense mutation in the SGSH gene [Bhaumik et al., Glycobiology, 9(12):1389-1396 (1999)] as described in the examples below.

Example 9

Figure 6:
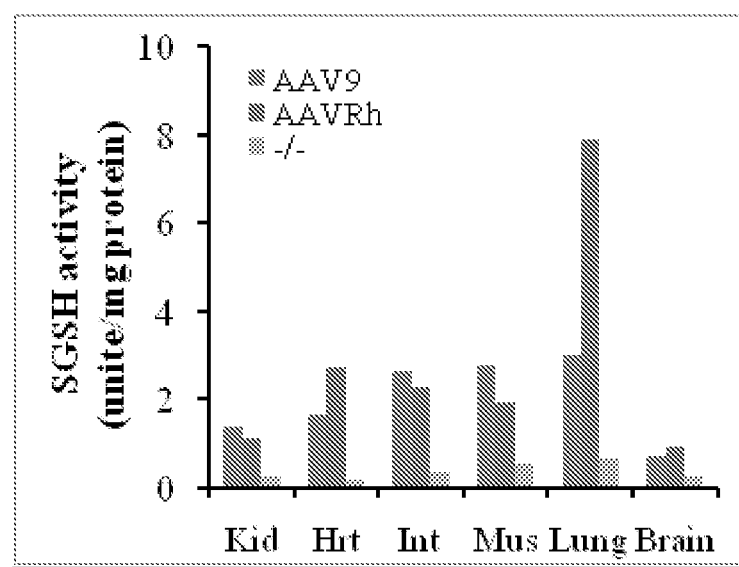
FIG. 6 shows rAAV9-mediated expression of functional rSGSH in tissues of treated MPSIIIA mice. For each tissue, AAV9, rh74 and untreated result bars are respectively shown from left to right.
Figure 6:
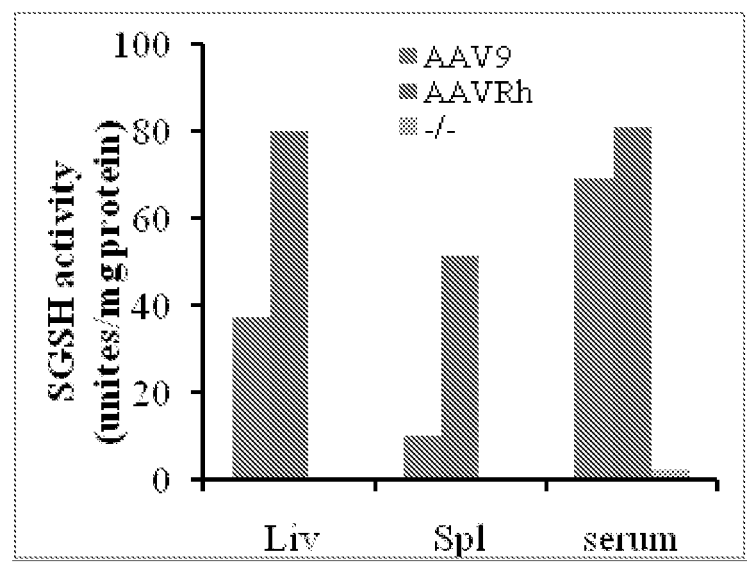
Figure 7:
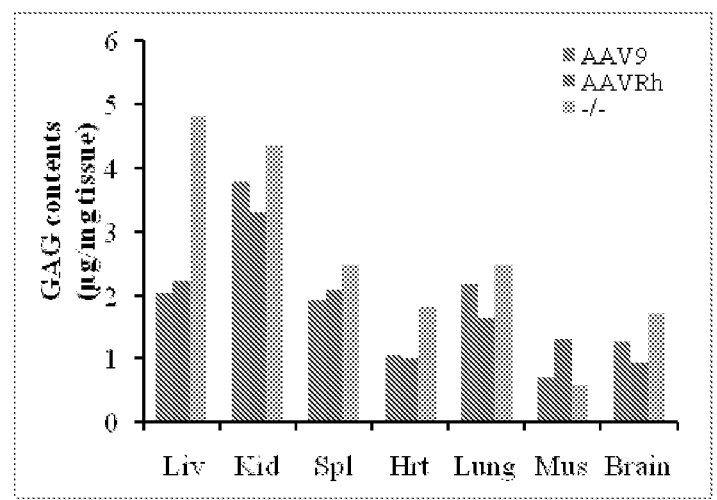
FIG. 7 shows a significant reduction of GAG content in tissues of treated MPSIIIA mice. For each tissue, AAV9, rh74 and untreated result bars are respectively shown from left to right.

MPS IIIA mice were injected at 10 weeks of age with $5 \times 10^{12}$ vgp/kg) of scAAV-U1a-hSGSH vector encapsidated in either AAV9 or AAVrh74 serotype. At 10 days post-injection, the mice were euthanized and assays were performed to determine the effects of the treatment.

hSGSH transgene expression was assayed. Tissues analyzed included kidney (Kid), heart (Hrt), intestine (Int), skeletal muscle (Mus), lung, brain, Liver (Liv), spleen (Spl) and serum. FIG. 6 shows enzyme expression relative to untreated MPS IIIA mice at the same age (−/−). The scAAV-SGSH vectors reached the CNS and expressed the transgene within days of administration. FIG. 7 shows GAG content measured in the kidney (Kid), heart (Hrt), muscle (Mus), lung, brain, Liver (Liv) and spleen (Spl).

Sections of CNS and somatic tissues were stained with the lysosomal marker, Lamp1, revealing clearance of lysosomal storage pathology. Histopathology additionally revealed numerous clear vacuoles present in untreated mice but corrected in treated animals.

Example 10

The therapeutic effects of scAAV-SGSH treatment at a low vector dose were examined.

Vector was administered by tail vein injection in MPS IIIA mice at one month of age at an approximately 25-fold lower dose than in Example 9. MPS IIIA mice were treated with $1.7 \times 10^{11}$ vgp/kg scAAV9-U1a-hSGSH or $2.7 \times 10^{11}$ vgp/kg scAAVrh74-U1a-hSGSH vector.

At three months post-injection, expression of SGSH in the CNS was observed by immunofluroescence staining. Correction of astrocytocis, a hallmark of neuroinflamation associated with MPS IIIA pathology, was also observed.

Figure 8:
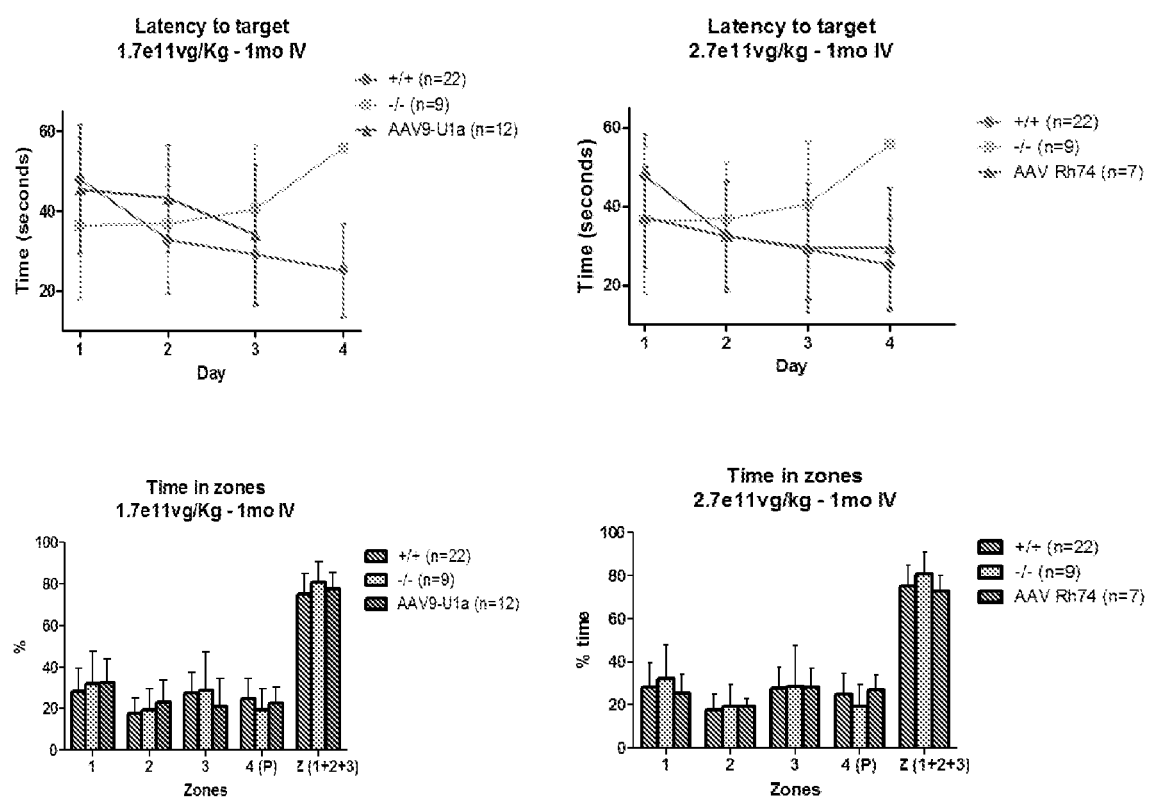
FIG. 8 shows an improvement in cognitive behavior assays after treatment of one-month old MPSIIIA mice with low dose scAAV9 or rh74-U1a-SGSH. In the lower graphs, for each tissue, untreated, wild type and either AAV9 or rh74 result bars are respectively shown from left to right.

At 7-7.5 months age, the animals were tested for learning ability in the Morris water maze. As shown in FIG. 8, compared to untreated controls, treated animals were similar to wt mice in their latency to locate the hidden platform (upper charts) and spent more time in the zone (4) where the platform had been in the previous tests when the platform was removed (lower charts).

Example 11

Therapeutic effects of scAAV treatment at high dose at late stage of disease were also examined.

MPS IIIA mice were treated with a high dose ($5 \times 10^{12}$ vgp/kg) of scAAV9-U1a-hSGSH vector at 6 months of age, after significant neuropathology had already developed. At 7-7.5 months age, the animals were tested for learning ability in the Morris water maze. At 7.5 months of age, the mice were euthanized and tissues assayed for glycosaminoglycan (GAG) content. Tissues analyzed include liver (Liv), kidney (Kid), heart (Hrt), brain, spleen (Spl), lung, skeletal muscle, and intestine.

Figure 9:
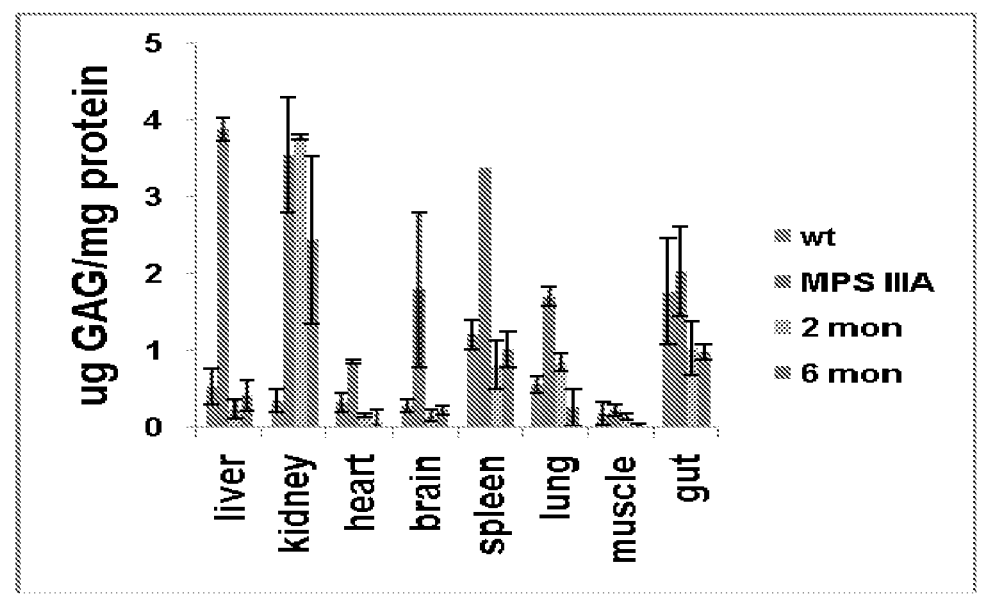
FIG. 9 shows a significant reduction of GAG content in tissues of MPSIIIA mice treated at 2 or 6 months of age. For each tissue, wild type, untreated, two-month and six-month result bars are respectively shown from left to right.
Figure 10:
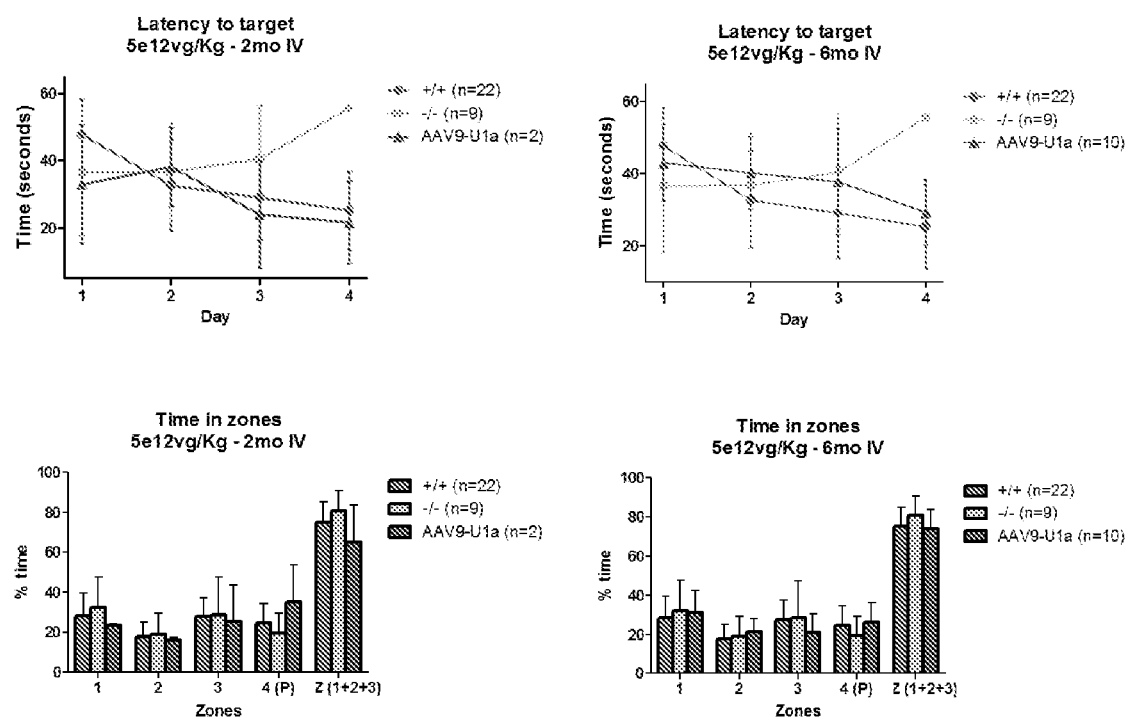
FIG. 10 shows an improvement in cognitive behavior assays after treatment of two- or six-month old MPSIIIA mice with high dose scAAV9 or rh74-U1a-SGSH. In the lower graphs, for each tissue, untreated, wild type and either AAV9 or rh74 result bars are respectively shown from left to right.

FIG. 9 shows clearance of accumulated GAGs in different tissues, including CNS. FIG. 10 shows, compared to untreated controls, treated animals were similar to wt mice in their latency to locate the hidden platform (upper charts) and spent more time in the zone (4) where the platform had been in the previous tests when the platform was removed (lower charts).

While the present invention has been described in terms of various embodiments and examples, it is understood that variations and improvements will occur to those skilled in the art. Therefore, only such limitations as appear in the claims should be placed on the invention.

All documents referred to in this application are hereby incorporated by reference in their entirety.

We claim:

1. A method of treating mucopolysaccharidosis IIIB (MPS IIIB) in a patient in need thereof comprising:
   (i) intravenously administering to the patient about $1\times10^{13}$ to about $1\times10^{16}$ vg/kg of a recombinant adeno-associated virus 9 (rAAV9) comprising a single-stranded genome expressing an α-N-acetylglucosaminidase (NAGLU) polynucleotide, wherein the rAAV9-NAGLU genome consists essentially of the polynucleotide sequence of SEQ ID NO: 5; and
   (ii) expressing the encoded NAGLU polypeptide in neurons, glia cells, and endothelial cells of the central nervous system of the patient;
   wherein the administration and expression are effective to:
   (a) alleviate lysosomal storage lesions in the central nervous system, peripheral nervous system and other somatic tissues,
   (b) alleviate neuropathology, astrocytosis and/or neurodegeneration in the central nervous system and peripheral nervous system, and
   (c) restore α-N-acetylglucosaminidase (NAGLU) activity in somatic tissues;
   wherein mannitol is not administered to the patient prior to administering the rAAV9.

2. The method of claim 1, further comprising testing the patient for neuroinflammation after the rAAV9 has been administered.

3. The method of claim 1, further comprising testing for systemic expression of the polynucleotide in the peripheral central nervous system of the patient.

4. The method of claim 1, comprising administering about $1\times10^{13}$ vg/kg of the rAAV9.

5. The method of claim 1, comprising administering about $1\times10^{14}$ vg/kg of the rAAV9.

6. The method of claim 1, comprising administering about $1\times10^{15}$ vg/kg of the rAAV9.

7. The method of claim 1, comprising administering about $1\times10^{16}$ vg/kg of the rAAV9.

* * * * *